United States Patent [19]

Drescher-Krasicka et al.

[11] Patent Number: 5,406,849
[45] Date of Patent: Apr. 18, 1995

[54] METHOD AND APPARATUS FOR DETECTING GUIDED LEAKY WAVES IN ACOUSTIC MICROSCOPY

[75] Inventors: Ewa Drescher-Krasicka; John A. Simmons, both of Gaithersburg, Md.

[73] Assignee: The United States of America, as represented by the Secretary of Commerce, Washington, D.C.

[21] Appl. No.: 922,845

[22] Filed: Jul. 31, 1992

[51] Int. Cl.⁶ .................................................. G01N 29/06
[52] U.S. Cl. ........................................ 73/588; 73/606; 73/627
[58] Field of Search .................. 73/606, 588, 607, 620, 73/627

[56] References Cited

U.S. PATENT DOCUMENTS

| H924 | 6/1991 | Chimenti | 73/627 |
|---|---|---|---|
| 3,585,851 | 6/1971 | Walther | 73/67.8 |
| 3,942,361 | 3/1976 | Rath et al. | 73/67.7 |
| 4,012,951 | 3/1977 | Kessler | 73/67.6 |
| 4,322,974 | 4/1982 | Abele et al. | 73/602 |
| 4,459,852 | 7/1984 | Chubachi et al. | 73/606 |
| 4,503,708 | 3/1985 | Kino et al. | 73/628 |
| 4,531,410 | 7/1985 | Crostack | 73/603 |
| 4,541,281 | 9/1985 | Chubachi et al. | 73/606 |
| 4,570,487 | 2/1986 | Gruber | 73/624 |
| 4,655,083 | 4/1987 | Chubachi | 73/606 |
| 4,658,649 | 4/1987 | Brook | 73/624 |

(List continued on next page.)

OTHER PUBLICATIONS

R. N. Thurston, "Elastic Waves in Rods and Clad Rods," (review paper) J. Acousti. Soc. Amer. 64 (1), 1–37, Jul. 1978.

C. K. Jen, A. Safaai-Jazi, and G. W. Farnell, "Leaky Modes in Weakly Guiding Fiber Acoustic Waveguides," IEEE Trans. Sonics, Ultrasonics, vol. UFF-C-33, No. 6, 634–643, Nov. 1986.

A. Safaai-Jazi, C. K. Jen, and G. W. Farnell, "Analysis of Guiding Fiber Acoustic Waveguide," IEEE Trans. Ultrasonic Ferroelectronics, Freq. Contr., vol. UFF-C-33, No. 1, 59–68, (Jan. 1986).

J. D. Achenback, "Wave Propagation in Elastic Solids," Editors: H. A. Lauwerier, W. T. Keiter, Sect. 6.5, vol. 16, North-Holland Publishing Co., Amsterdam, London (1973) (pp. 211–218).

A. Schoch, "Seitliche Versetzung eines total reflekozienten Strahls bei Ultraschallwellen," Acustica, 2. vol. 18–19 (1952).

L. V. Ahlfans, "Complex Analysis," III edition, Editors: G. Springev and E. H. Spenier, McGraw-Hill Book Co., New York (1979) (pp. 256–261).

(List continued on next page.)

Primary Examiner—Hezron E. Williams
Assistant Examiner—Rose M. Finley
Attorney, Agent, or Firm—Jacobson, Price, Holman & Stern

[57] ABSTRACT

An apparatus and method for non-destructive examination of an interface within a body between two separate elements of the body wherein an acoustic microscope (124) has an ultrasonic transmitter (114) for directing ultrasonic waves at an angle to a body (1) and an interface (122) within the body between an outer part (3) and an inner part (2), an acoustic receiver (116) in spaced relationship to the transmitter (114) for receiving acoustic leaky waves from the interface (122), and a supporting device for supporting the transmitter and receiver for simultaneous scanning movement relative to the body at the same scanning speed. The body to be examined may be supported immersed in a liquid such as water (120) in a tank (121) so that the ultrasonic waves from the transmitter are directed at a predetermined angle depending on the materials of the separate elements and pass through the liquid and the outer part before impinging on the interface in the body to be examined.

21 Claims, 26 Drawing Sheets

U.S. PATENT DOCUMENTS

| | | | |
|---|---|---|---|
| 4,674,333 | 6/1987 | Jindo et al. | 73/606 |
| 4,674,334 | 6/1987 | Chimenti et al. | 73/627 |
| 4,702,112 | 10/1987 | Lawrie et al. | 73/629 |
| 4,788,866 | 12/1988 | Tanimoto et al. | 73/606 |
| 4,821,728 | 4/1989 | Ledley | 73/624 |
| 4,866,986 | 9/1989 | Cichanski | 73/606 |
| 5,079,952 | 1/1992 | Nakaso et al. | 73/624 |
| 5,225,148 | 7/1993 | Desruelles | 73/627 |

OTHER PUBLICATIONS

M. Onoe, H. D. McNiven and R. D. Mindlin, "Dispersion of Axially Symmetric Waves in Elastic Rods," J. Appl. Mech. 29, 729–734, Dec. 1962.

E. Drescher-Krasicka, J. A. Simmons, and H. N. G. Wadley, "Guided Interface Waves," Review of Progress on QNDE, vol. 6B, 1129–1136, Editors: D. Thompson, D. E. Chimenti, LaJolla 1978.

H. N. G. Wadley, et al., "Composite Materials Interface Characterization," NBS Internal Report 87-3630,. 1 Gaithersburg (1987) (abstract only).

J. A. Simmons, et al., "Ultrasonic Methods for Characterizing the Interface in Composites," Review of Progress in QNDE, vol. 7, Ed: D. O. Thompson and D. E. Chimenti Plenum Press, New York, London, (1987). pp. 893–901.

D. C. Gazis, "Three-Dimensional Investigations of the Propagagation of Waves in Hollow Circular Cylinders," I. Analytic Foundation, J.A.S.A. 81, 568–573 May 1959 (vol. 31, No. 5).

D. A. Lee and D. M. Corbly, "Use of Interface Waves for Non-destructive Inspection," IEEE Trans. Sonics, Ultrasonic, vol. SU-24 No. 3, (May 1977) pp. 206–212.

G. N. Watson, "A Treatize on the Theory of Bessel Functions," II edition, Cambridge University Press, Cambridge (1966) (pp. 76–80).

F. W. J. Olver, "Bessel Functions of Integer Order," editors: M. Abramowitz and I. Stegum, N. B. (28b)S. Applied Math. Series 55, Washington, D.C. (1964).

L. Tamir and H. L. Bertoni, "Lateral Displacement of Optical Beams at Multilayered Periodic Structures," J. Opt. Soc. Amer., vol. 61, No. 10, 1397–1413, Oct. 1971.

B. A. Auld, "Acoustic Fields and Waves in Solids," vol. 1, 221–223, ed. John Wiley & Son, New York, London, Sydney, Toronto (1973).

J. L. Synge, "Flux of Energy for Elastic Waves in Anisotropic Media," Proc. R. I. A. vol. 58, Section A, Nov. 1956.

M. J. Lighthill, "Group Velocity," J. Inst. Meths. Applics, 1, 1–28 (1965). (c.f., especially fig. 6 where the 0.31 Poisson ratio 0.296 value for SiC).

PARTICLE DISPLACEMENT $\rho = \text{Re}(Ae^{i\omega t} e^{-i\omega t(\alpha - i\beta)})$

FIG. 37(a)

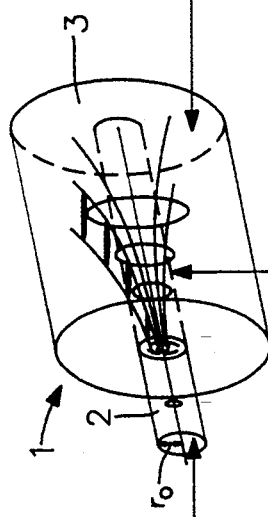

IN THE CLADDING $u_C \equiv v_{Ci} = (v_{C1}, v_{C2}, v_{C3}) = Rl(Q_C(r)e^{ik(vt-z)})$ number subscripts refer to Cartesian coordinates
v=complex mode velocity
k=complex wave number
r,z=radical and axial coordinates $$0 = \sum_{j,k,l} \frac{\partial}{\partial x_j}\left[(C_C)_{ijkl}\frac{\partial u_{Ci}}{\partial x_j}\right] - \rho_C \frac{\partial^2 u_{Ci}}{\partial t^2}$$

$(C_C)_{ijkl} = \lambda_C \delta_{ij}\delta_{kl} + \mu_C(\delta_{il}\delta_{jk}+\delta_{ik}\delta_{jl})$ $\rho_C$=cladding density $a_C$=longitudinal velocity in cladding=$\sqrt{\frac{\lambda_C + 2\mu_C}{\rho_C}}$ $b_C$=shear velocity in cladding=$\sqrt{\frac{\mu_C}{\rho_C}}$ $A_C = \pm\sqrt{1-\frac{v^2}{a_C^2}}$ $B_C = \pm\sqrt{1-\frac{v^2}{b_C^2}}$

IN THE ROD $u_R \equiv v_{Ri} = (v_{R1}, v_{R2}, v_{R3}) = Rl(Q_R(r)e^{ik(vt-z)})$ number subscripts refer to Cartesian coordinates
v=complex mode velocity
k=complex wave number
r,z=radical and axial coordinates $$0 = \sum_{j,k,l} \frac{\partial}{\partial x_j}\left[(C_R)_{ijkl}\frac{\partial u_{Ri}}{\partial x_j}\right] - \rho_R \frac{\partial^2 u_{Ri}}{\partial t^2}$$

$(C_R)_{ijkl} = \lambda_R \delta_{ij}\delta_{kl} + \mu_R(\delta_{il}\delta_{jk}+\delta_{ik}\delta_{jl})$ $\rho_R$=rod density $a_R$=longitudinal velocity in rod=$\sqrt{\frac{\lambda_R + 2\mu_R}{\rho_R}}$ $b_R$=shear velocity in rod=$\sqrt{\frac{\mu_R}{\rho_R}}$ $A_R = \pm\sqrt{1-\frac{v^2}{a_R^2}}$ $B_R = \pm\sqrt{1-\frac{v^2}{b_R^2}}$

FIG. 37(b)

AT THE INTERFACE $$\mathrm{Det}\left[\begin{array}{cc} \rho_C\left[(v^2-2b_C^2)K_0(A_Ck)-2b_C^2 c A_C K_1(A_Ck)/k\right]-\rho_C b_C^2 \begin{bmatrix} \dfrac{2\rho_C b_C^2 A_C K_1(B_Ck)}{K_0(A_Ck)} \\ A_C K_1(A_Ck) \end{bmatrix} & \rho_C(2b_C^2-v^2)K_1(B_Ck) \\ \dfrac{2\rho_R b_R^2 A_R I_1(B_Rk)}{-I_0(A_Rk)} & \begin{bmatrix} B_C K_0(B_Ck)+K_1(B_Ck)/k \\ K_1(B_Ck) \end{bmatrix} \\ \rho_R\left[(2b_R^2-v^2)I_0(A_Rk)-2b_R^2 A_R I_1(A_Rk)/k\right] & 2\rho_R b_R^2 \begin{bmatrix} \rho_R(2b_R^2-v^2)I_1(B_Rk) \\ B_R I_0(B_Rk)-I_1(B_Rk)/k \\ -B_R I_0(B_Rk) \\ I_1(B_Rk) \end{bmatrix} \end{array}\right]=0$$

$K \equiv r_0 k = \dfrac{2\pi r_0 f}{2}$, $f=$ frequency $I_0 I_1 K_0 K_1 =$ modified Bessel functions

METHOD AND APPARATUS FOR DETECTING GUIDED LEAKY WAVES IN ACOUSTIC MICROSCOPY

BACKGROUND OF THE INVENTION

This invention relates to an acoustic microscope technique and apparatus for non-destructive testing of an interface between two materials by spatially scanning ultrasonic waves through the material to the interface and detecting resultant leaky waves produced at the interface for determining flaws in the interface.

The construction and operation of acoustic microscopes for non-destructive testing is known from U.S. Pat. Nos. 4,459,852; 4,503,708; 4,658,649; 4,541,281; 4,655,083; and 5,079,952, for example. The teachings of these patents are incorporated herein by reference as showing examples of acoustic microscopes and components thereof which may be useful in carrying out the instant invention.

When a guided ultrasonic interface wave travels along the interface between two materials it radiates acoustic energy from each point on the interface, and forms a displacement field at the outer surface of the material.

The acoustic microscope technique for examining interfaces is noninvasive and nondestructive. Spatial scanning of the radiating energy passing through the cladding material produces an image of the interface. The resolution of the image depends on the propagation parameters of the leaky waves. An asymptotic leakage angle, the phase and group velocity (energy flow), and the attenuation (the imaginary part of propagation) vary with the wavelength for a fixed diameter rod. These parameters were calculated for each radial-axial mode for the dispersive geometry of an infinitely thick cladded rod. A variety of wave behavior was verified experimentally on samples of silicon carbide rods and steel rods embedded in an aluminum matrix.

The following is a brief review of the experimental achievements in the field of leaky, axisymmetric modes in infinitely thick clad rods.

Application of Stoneley and leaky interface waves are known for the purpose of evaluating the physical and mechanical properties of interfaces because these waves are ideal for the detection of disbonds and inclusions at interfacial bondlines. E. Drescher-Krasicka, J. A. Simmons, and H. N. G. Wadley, "Guided Interface Waves," QNDE 6B, 1129–1136 (1986); W. L. Pilant, Bull. Seism. Soc. Am. 62, 285–299 (1972); R. Yamaguchi and K. Sato, Bull. Earthquake Res. Inst. Tokyo Univ. 33, 549–559 (1955); D. A. Lee and D. M. Corbly, IEEE Trans. Sonics Ultrason. SU-24, 206–212 (1977). Others have described the importance of leaky and Stoneley waves in ultrasonic signal processing devices. Bertoni has related Stoneley and leaky wave propagation characteristics to the effect of the coupling layer on the efficiency of wedge transducers. Experimental observations of ultrasonic waves at solid-solid interfaces have been reported as shown by R. O. Claus and C. H. Palmer, Appl. Phys. Lett. 31, 547 (1977); R. O. Claus, First Int. Symp. Ultrason. Matls. Charact., Gaithersburg, Md. (1978); R. O. Claus and R. A. Kline, J. Appl. Phys. 50, 8066 (1979); H. A. Kunkel and B. A. Auld in Ultrasonic Symposium Proceedings, Atlanta, edited by McAvoy (IEEE, New York, 1983); K. D. Bennett, S. J. Hanna, and R. O. Claus, in IEEE 1985 Ultrasonic Symposium Proceedings, San Francisco, edited by B. R. McAvoy (IEEE, New York, 1985); B. S. Jackson, R. G. May, and R. O. Claus, in Proceedings of IEEE Southestcon 84, edited by B. R. McAvoy (IEEE, New York, 1985); K. Tajima, Electron. Lett. (UK) 27(3), 251–253 (1991); F. Leomy, et al., J. Appl. Phys. 67, 1210–1218 (1990); and S. I. Rokhlin, J. Phys. (Paris) 46, (C-10), 805–808 (1985).

Mode conversion has been used to and from Rayleigh surface acoustic waves (SAW) to generate and detect leaky interface waves on steel-aluminum and titanium-aluminum planar and cylindrical interfaces. It has been shown that an interface wave guided by a thin polymer film between two solids is capable of localizing the energy of elastic waves near the interface. In most of these applications, optical receivers were used as the detectors of the interface waves. S. I. Rokhlin, M. Hefets, and M. Rosen, J. Appl. Phys. 51, 7 (1980); S. I. Rokhlin, M. Hefets, and M. Rosen, J. Appl. Phys. 52, 4 (1981).

Ultrasonic measurements on a cylindrical model sample have been compared with the theoretical calculations of the dispersion relation for weakly leaky radial-axial aluminum-steel interface modes and good agreement was found between calculated and measured values. E. Drescher-Krasicka, J. A. Simmons, and H. N. G. Wadley, "Guided Interface Waves,)" QNDE 6B 1129–1136 (1986); J. A. Simmons, H. N. Wadley, E. Drescher-Krasicka, M. Rosen and T. M. Hsieh, "Ultrasonic Methods for Characterizing the Interface in Composites," QNDE 7 XX-XX (1987); H. N. G. Wadley, J. Simmons, and E. Drescher-Krasicka, "Ultrasonic Propagation at Cylindrical Metal-Ceramic Interfaces in Composites," in Proceedings of the MRS Symposium High Temperature Composites, Reno, Nevada, edited by F. Lemkey et al. (MRS, Pittsburgh, 1988); E. Drescher-Krasicka, J. A. Simmons, and H. N. Wadley, "Fast Leaky Modes on Cylindrical Metal-Ceramic Interfaces," QNDE 9A 173–181 (1989).

BRIEF SUMMARY OF THE INVENTION

The object of this invention is to provide an apparatus and method for nondestructive examination of at least one interface within a body between at least two separate elements of the body.

A further object of the invention is to provide such an apparatus utilizing an acoustic microscope having an ultrasonic transmitter for transmitting ultrasonic waves toward the body to be examined and an ultrasonic receiver for receiving acoustic leaking energy from the interface.

A further object of the invention is to provide an apparatus and method for determining flaws in a body consisting of two materials having an interface therebetween by utilizing an acoustic microscope for spatially scanning ultrasonic waves through the material to the interface and detecting resultant acoustic leaky waves produced at the interface for determining the flaws.

The above objects are achieved by the instant invention by supporting the body to be examined immersed in a liquid in a container, supporting the ultrasonic transmitter and receiver in relative spaced relationship for simultaneous scanning movement with respect to the body at the same scanning speed whereby ultrasonic waves produced by the transmitter penetrate one of the elements of the body and propagate leaky waves at the interface which are detected by the receiver. The transmitter and receiver are adjustably mounted so that the transmitted waves are directed at a predetermined transmitted wave angle relative to the interface dependent upon the materials of the separate elements of the body being tested, and the leaky waves from the interface are detected at a leakage angle relative to the interface. The transmitted wave angle relative to the interface, i.e., the angle at which the ultrasonic waves are directed from the transmitter to the interface, is in a predetermined range so that the leakage angle is in the range of approximately 13° to 19°. The transmitted wave angle may also be adjusted to a predetermined angle so that the leakage angle is approximately 55°.

The method of this invention is carried out by positioning an ultrasonic transmitter of an acoustic microscope relative to an interface within a body of at least two materials, exciting the ultrasonic transmitter to produce transmitted ultrasonic waves, directing the transmitted waves toward the interface within the body being examined, positioning the ultrasonic receiver with respect to the transmitter for receiving leaking acoustic energy from the interface at an angle thereto produced by the transmitted waves and moving the transmitter and receiver simultaneously relatively to the body being examined at the same scanning speed so that the transmitted waves progagate leaky waves at the interface which radiate acoustic energy at an angle from each point in the interface, and detecting the leaky waves by the receiver. In one example, the transmitted wave angle is adjusted in positions within a predetermined range so that the leakage angle propagated thereby is in the range of approximately 13° to 19°. In another example, the two separate elements may be aluminum and silicon carbide and the predetermined transmitted wave angle is in a range so that the leakage angle propagated is approximately 55°.

In addition, in carrying out the method and in using the apparatus, the receiver lens of the receiver and the transmitter are preferably substantially immersed in the liquid in the container. The leaky waves detected by the receiver produce signals which are transmitted to the acoustic microscope which in conjunction with a computer produces an acoustic image of the energy leaking from the body being examined. A stepping motor is also electrically connected to the computer so that it is controlled thereby to simultaneously move the transmitter and receiver in accordance with the invention.

BRIEF DESCRIPTION OF THE DRAWINGS

The invention will now be described in greater detail with reference to the accompanying drawings, wherein:

FIGS. 37(a), 37(b) 33(c) together show a flowchart illustrating an example of the operation of the embodiment of FIG. 29.

DETAILED DESCRIPTION OF PREFERRED EMBODIMENTS

Since a clad rod consists of the conjunction of a bare rod with an infinite cladding, there exists a relationship between leaky modes and the modes in a bare rod or in an infinite material with a cylindrical tunnel. As long as the density of the rod is nonzero, most leaky modes are leaky rod modes.

The attenuation factor is an important experimental parameter since it predicts which modes have sufficiently low attenuation for easy detection. Modes with measurable attenuation usually do not exceed 18 to 22 dB/mm, depending on the sensitivity of the receiver.

Steel Rod in Aluminum Cladding

Aluminum matrix-steel rod interface models have been studied experimentally and the results compared with theoretical calculations. Two fabrication methods were used to prepare the samples of the steel-aluminum cylindrical interface models: shrink fitting and casting. The first model shown in FIG. 1 was composed of a 3.2 mm radius 316 stainless steel rod 2, shrink fitted into a 2024 aluminum alloy cylinder 3. Shrink fitting created a very tight cylindrical interface between these two materials because of their large difference in thermal expansion coefficients.

Figure 2:
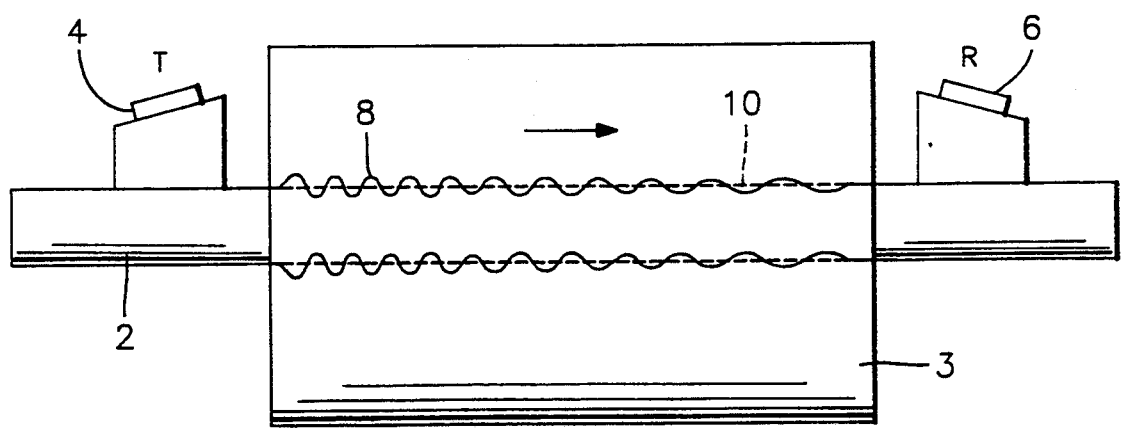
FIG. 2 is a schematic view of the sample of FIG. 1 showing the transmitter T and the receiver R attached to the sample.

Exploring other possible methods, it was found that interface waves were best generated by the conversion of rod surface acoustic waves (SAW). Polymethylmethacrylate wedges as shown in FIG. 2 were used to generate and detect these ultrasonic surface waves over a range of frequencies. Transmitter 4 (T) and receiver 6 (R) were attached to the opposite ends of steel rod 2. The interface wave 8 was generated by mode conversion from the SAW propagating along the rod. At the other end of the sample the interface wave recovered into the surface acoustic wave where it was detected by the receiver 6. Knowing the surface wave velocities for the applied frequencies on the steel rod, and measuring the delay time in the two wedges, the velocity of the interface wave along the Al-steel interface 10 was obtained.

Figure 1:
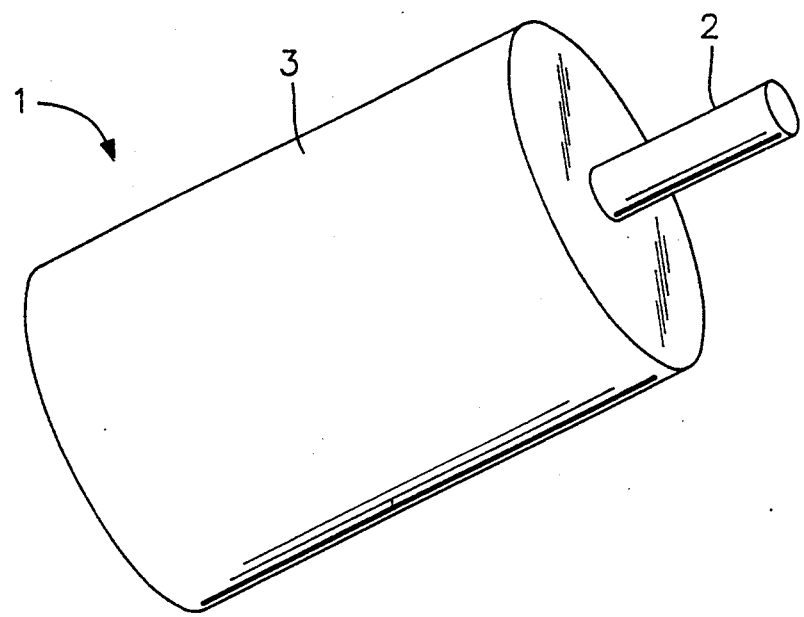
FIG. 1 is a perspective view of a model sample of a steel rod shrink fitted into an aluminum alloy cylinder to produce an aluminum-steel cylindrical interface.
Figure 3:
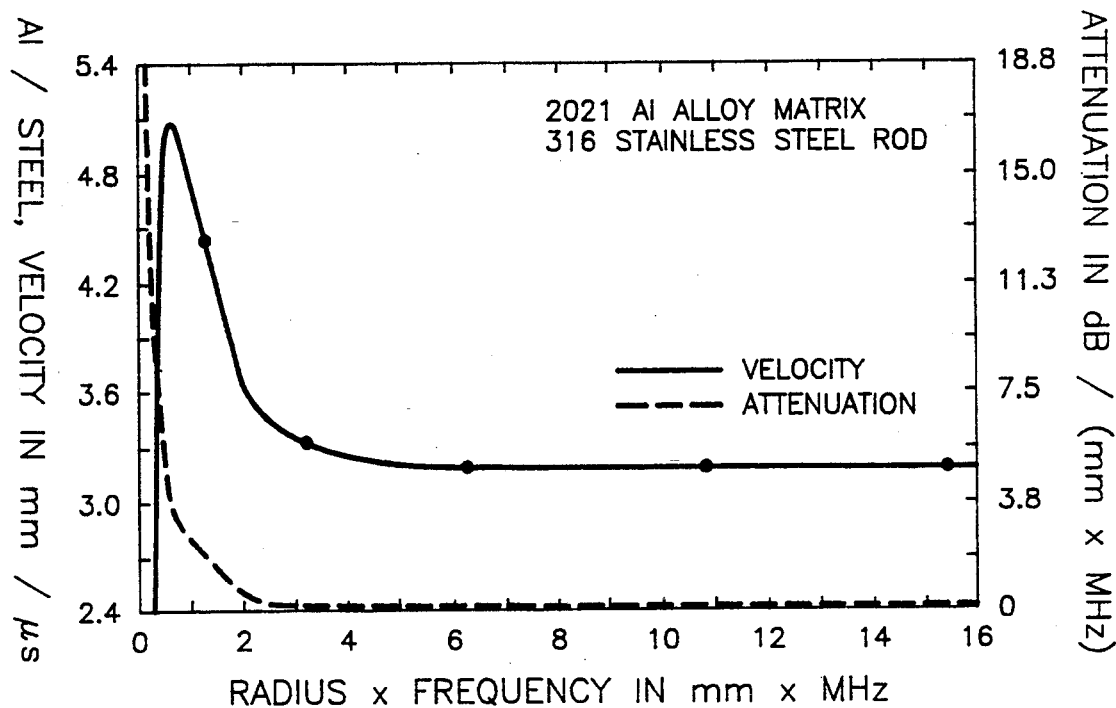
FIG. 3 is a graph showing the interface wave velocity (as separate points) measured as a function of frequency for the samples shown in FIGS. 1 and 2.

FIG. 3 presents the interface wave velocities (as separate points) measured as a function of frequency for the sample shown in FIGS. 1 and 2. These can be compared with the curve of the theoretically predicted phase velocities. FIG. 3 shows a comparison between calculated (continuous line) and measured (points) phase velocity dependence on dispersion parameter (frequency X radius of the rod) for a radial axial shallow leaky mode at the aluminum steel interface. The experimental results were obtained for frequencies of 0.5, 1, 2, 3.5, and 5 MHz. The accuracy of the measurements was 35 m/s. Very good agreement between theory and experiment was obtained. In order to accurately measure phase velocity of interface waves as a function of frequency, different techniques for receiving the acoustic leaking energy were tried. For example, water and other acoustic couplants were tested, as well as different receiving techniques (EMATs, pin transducers, acoustic lenses).

Silicon Carbide Rod in Aluminum Cladding

Also shown were dispersion relations for leaky modes propagating at the interfaces of a silicon carbide rod embedded in aluminum cladding. In the dispersive region characterized by the wavelength being comparable to the radius of the rod, the radial-axial modes in the bar rod have the limiting cases of infinite phase velocity; leaky interface modes in the embedded rod always propagate with a finite phase velocity. This velocity can be measured directly at the interface.

Figure 4:
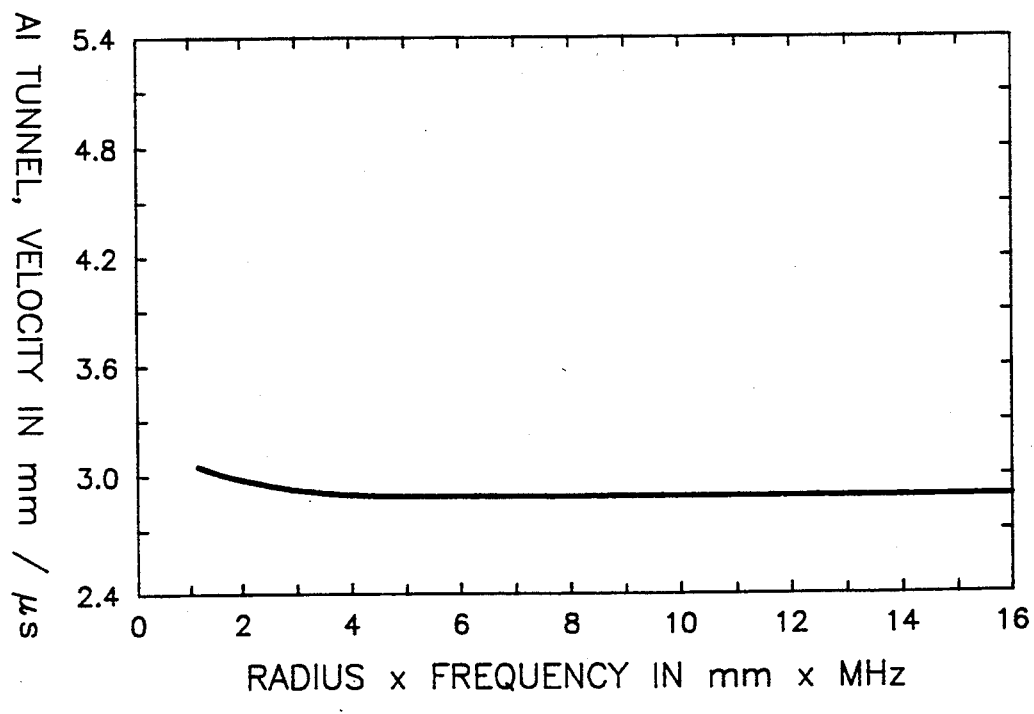
FIG. 4 is a graph showing the calculated dispersion curve for the radial displacement mode propagating axially along the aluminum tunnel for a sample of a silicon carbide rod in aluminum cladding.
Figure 5:
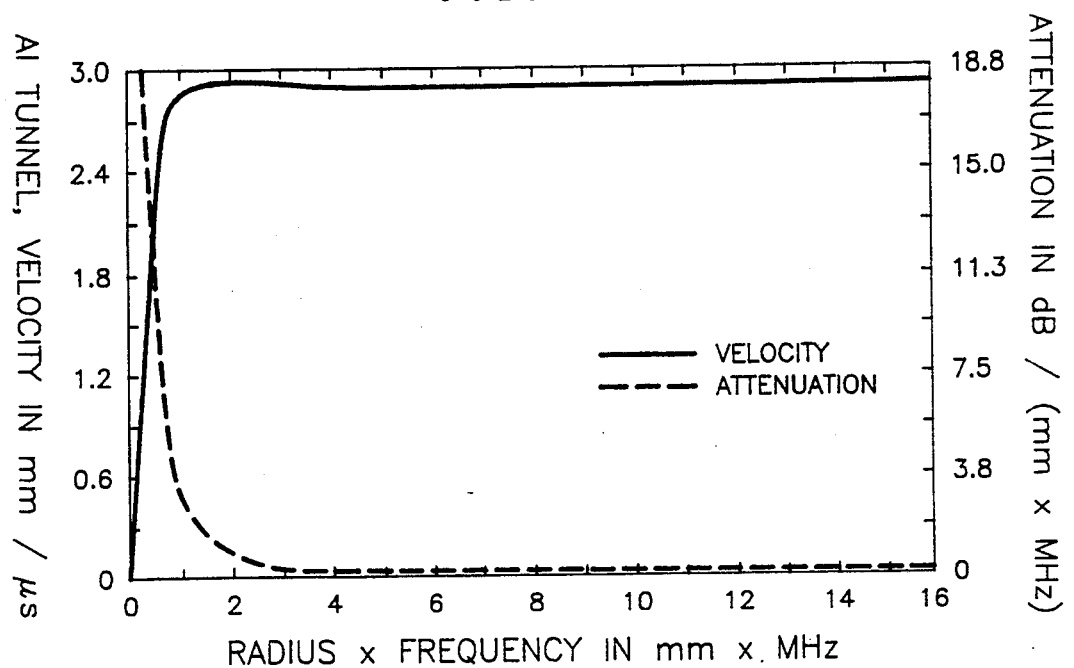
FIG. 5 is a graph showing an attenuated radio-axial mode in aluminum tunnel wherein the phase velocity is shown in the continuous line and the imaginery part of the velocity is shown in a dash line as a function of the dispersion parameter (frequency X-radius)
Figure 6:
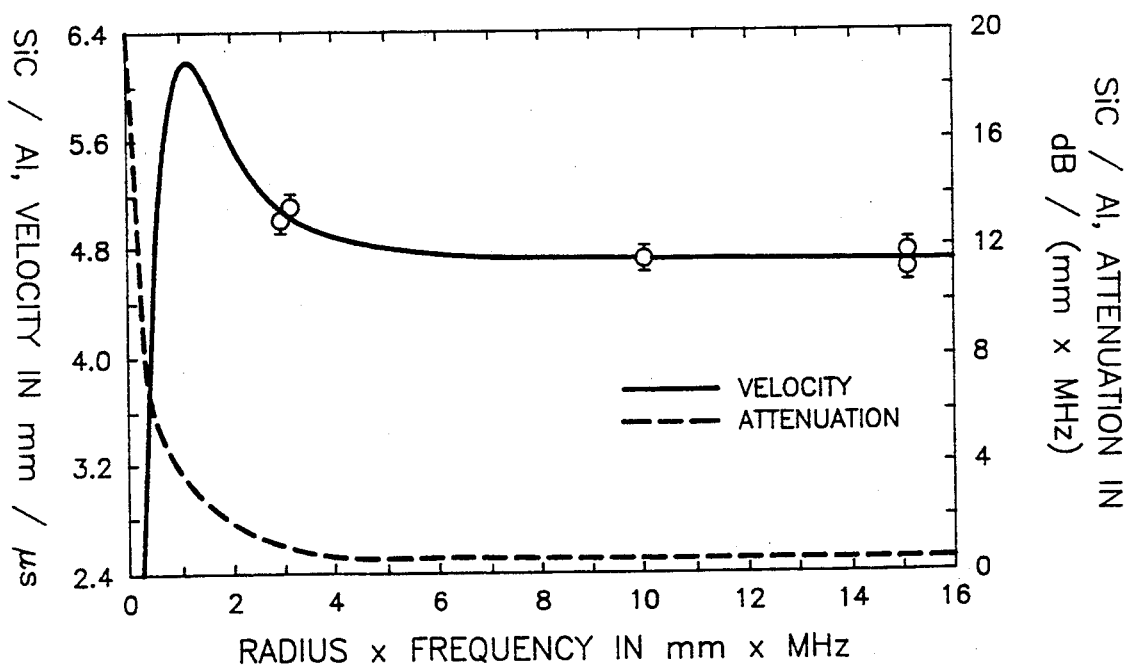
FIG. 6 is a graph showing dispersion behavior for an interface wave at the cylindrical aluminum-silicon-carbide interface, the calculated phase velocity shown in the continuous line and the attenuation shown in the dashed line as a function of the frequency x radius (dispersion parameter) of the rod, and shows a comparison between the calculated and measured (points) dispersion curve.
Figure 7:
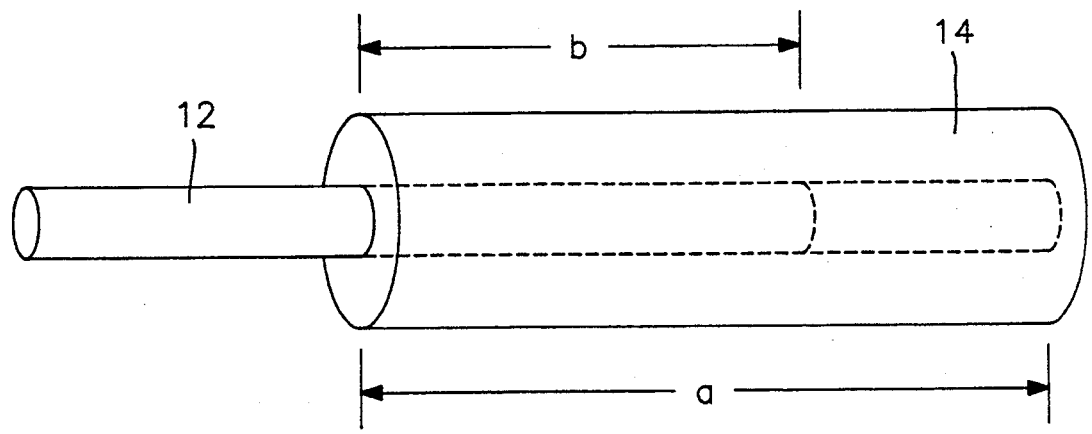
FIG. 7 shows a sample composed of a SiC rod embedded in an aluminum matrix.

The model aluminum matrix containing various SiC fibers was used as an example of a single cylindrical interface. In FIG. 4, the calculated dispersion curve for the radial displacement mode propagating axially along the aluminum tunnel is shown. This mode has a purely real root corresponding to an unattenuated mode. FIG. 5 shows a second radial-axial mode in the aluminum tunnel. This mode exhibits frequency-dependent attenuation. The measurements of these two tunnel modes were not accurate enough, due to difficulties with mode generation to compare the calculations with the experimental data. The dispersion behavior for an interface wave at the cylindrical aluminum-silicon carbide interface is shown in FIG. 6. The acoustic energy of leakage for this mode propagates through the matrix with a group velocity approaching the shear velocity in aluminum. FIG. 6 presents the measured velocities (points) along with the theoretical predictions (continuous line). The accuracy of the experiment was 60 m/s. An Al—SiC sample, as shown in FIG. 7, composed of a 3.2 mm radius SiC rod 12, shrink fitted into a 2024 aluminum cylinder 14, was used to test the theoretical velocity predictions. The length a of the aluminum cylinder is 50 mm and the length h of insertion of rod 12 is 30 mm. The bulk ultrasonic shear and longitudinal velocities, as well as the densities, were measured in the Al and SiC separately and the following results were used for the calculations: density of aluminum, $\rho_c = 2.77 \times 10^{-3}$ [g/mm$^3$]; longitudinal velocity of Al, $a_c = 6.323$ [mm/$\mu$]; shear velocity of Al, $b_c = 3.1$ [mm/$\mu$s], density of silicon carbide, $\rho_R = 3.2 \times 10^{-3}$ [g/mm$^3$]; longitudinal velocity of SiC, $a_R = 9.649$ [mm/$\mu$s], shear velocity of SiC, $b_R = 5.193$ [mm/$\mu$s].

Figure 8:
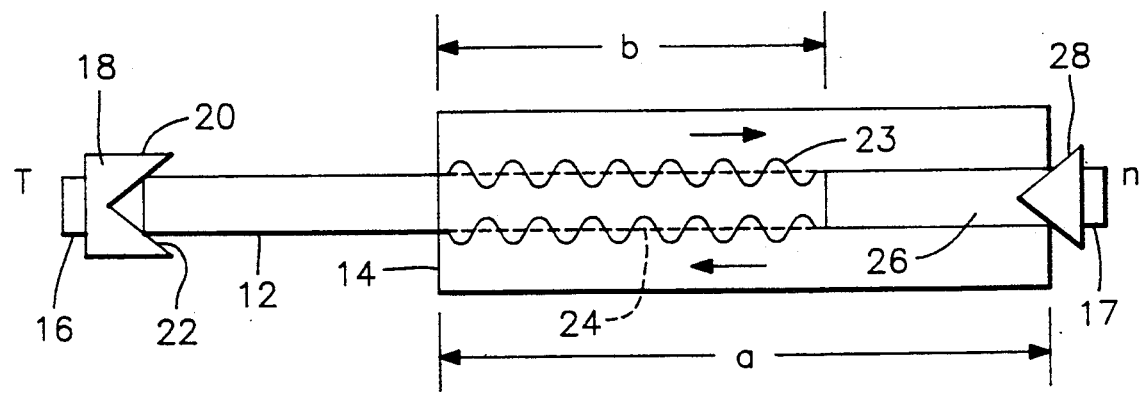
FIG. 8 is a schematic view showing the generation and detection of leaky radial-axial mode in the sample of FIG. 7.

The measurement technique used for the generation and detection of leaking radial-axial waves is schematically shown in FIG. 8. Transducers 16 of different frequency were used as transmitters T. These were placed on a concave aluminum waveguide 20. Only the circular edge 22 of the silicon carbide was in contact with the transmitting waveguide. The interface wave 23 was generated by mode conversion from a surface acoustic wave on the rod, which projected out from the matrix tunnel 24. At the other end of the interface, the interface wave reconverted into a surface acoustic wave and traveled along the aluminum tunnel 26, where it was detected by another aluminum waveguide 28 of convex curvature and a receiving R transducer 17 thereon.

The velocity of the interface wave along the Al—SiC interface is obtained by calculating the velocity of the surface wave on the silicon carbide rod and aluminum tunnel 26 separately, and measuring the delay time in the two waveguides. These preliminary results indicate that leaky interface waves can be propagated on metal-ceramic interfaces.

A theoretical search for radial-axial interface modes at the cylindrical SiC—Al interfaces produced more than 40 calculated roots, but only a few of these predicted modes are practical for experimental use.

Figure 9:
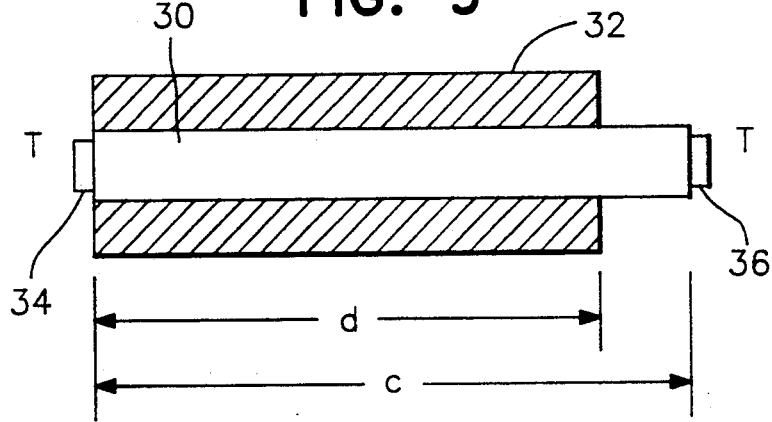
FIG. 9 is a cross-sectional schematic view showing a silicon-carbide-aluminum interface model sample prepared by hot isostatic pressing (HIP) having two identical shear wave transducers attached to the opposite ends of the SIC rod.

The attenuation of the acoustic energy leaking from the Al—SiC interface was measured at the outer surface of the aluminum matrix by use of a low-frequency acoustic microscope identified as Microscan System manufactured by Sonix, Inc. A leaky wave was excited at the interface and received by the acoustic lens focused at the surface of an aluminum cladding. The sample used in the acoustic microscope experiment is shown in FIG. 9. A silicon carbide rod 30 of radius $r = 3.065$ mm and length c of 58.35 mm was embedded in an aluminum matrix cylinder 32 having a diameter of 17.26 mm and length d of 50 mm. The sample was prepared by means of the hot isostatic pressing (HIP) method. The fabrication of high-quality cylindrical interfaces between aluminum matrices and silicon carbide rods was the subject of separate efforts. Several techniques were tried, including shrink fitting and casting in molds; however, when creating metal-ceramic interfaces, the best results were obtained by the HIP method.

Figure 10:
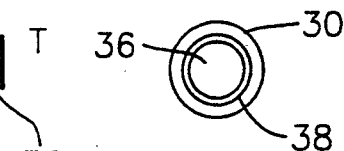
FIG. 10 is an end view of the rod element of FIG. 9.

Two identical 3-MHz shear wave transducers 34, 36 were attached to the two ends of the silicon carbide rod. The transducers were driven by a single frequency pulse applied to circular ring-shaped electrodes painted on their faces. This is a very efficient method for exciting surface waves at outer surfaces of the rod and, by mode conversion, interface waves along the cylindrical interface. The transducers attached to each end of the rod were used as transmitter and receiver, or as transmitters only. Circular ring-shaped electrodes 38 were painted on the faces of the transducers as shown in FIG. 10.

Figure 11:
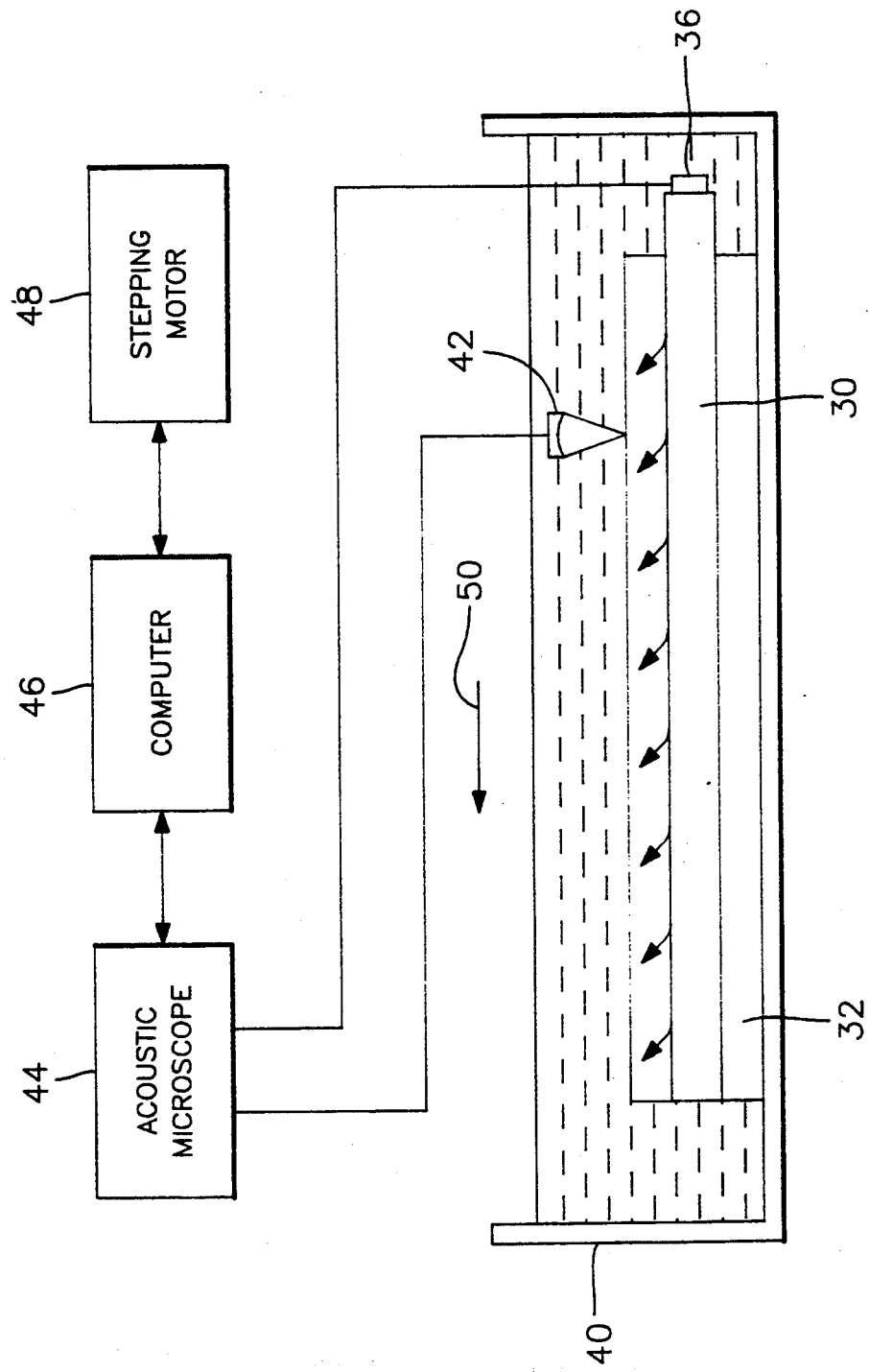
FIG. 11 is a schematic view for the detection of acoustic energy of leaking along the interface of a sample such as that shown in FIG. 7.

FIG. 11 is a schematic view of the ultrasonic experiment which shows a sample similar to FIG. 7 placed in a water tank 40. The movable acoustic lens 42 of acoustic microscope 44 focused at the outer surface of the aluminum sample 32 detected and registered the ultrasonic radiation from the progressing interface wave. Acoustic microscope 44 includes computer 46 and stepping motor 48 for operating the lens 42 moved in the direction of arrow 50. The low-frequency acoustic microscope lens focused at the surface of the cladding was used as a receiver. The transducer 36 (protected against water) excited the interface wave which propagated along the interface. The receiver moved along the Z direction. The sample used in the experiment is shown in FIG. 7. A spatial fast Fourier transform was used to separate various modes in the received signal. Windowing applied to the chosen wavelength permitted separation of the leaky mode.

Figure 12:
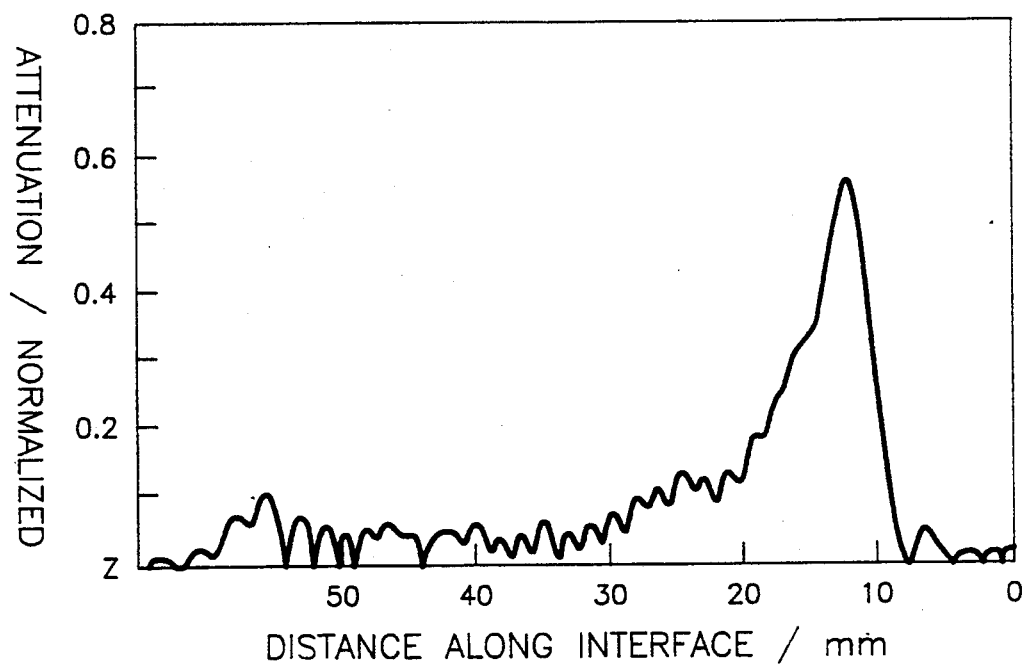
FIG. 12 is a curve of attenuation plotted against distance along the interface.

FIG. 12 shows the curve for attenuation plotted against distance along the interface for the experiment of FIG. 11, with the receiver moved in the Z direction as shown by the arrow 50.

Figure 13:
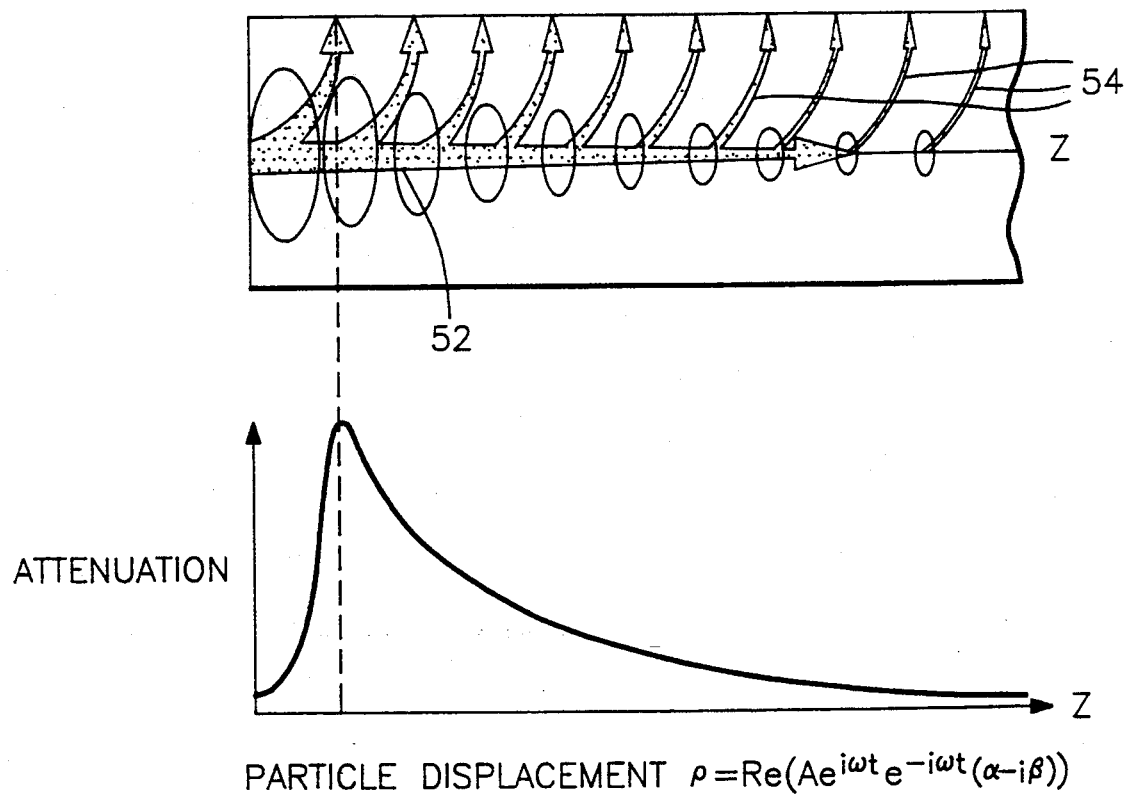
FIG. 13 is a schematic illustration of the energy flow pattern for leaky waves.
Figure 14:
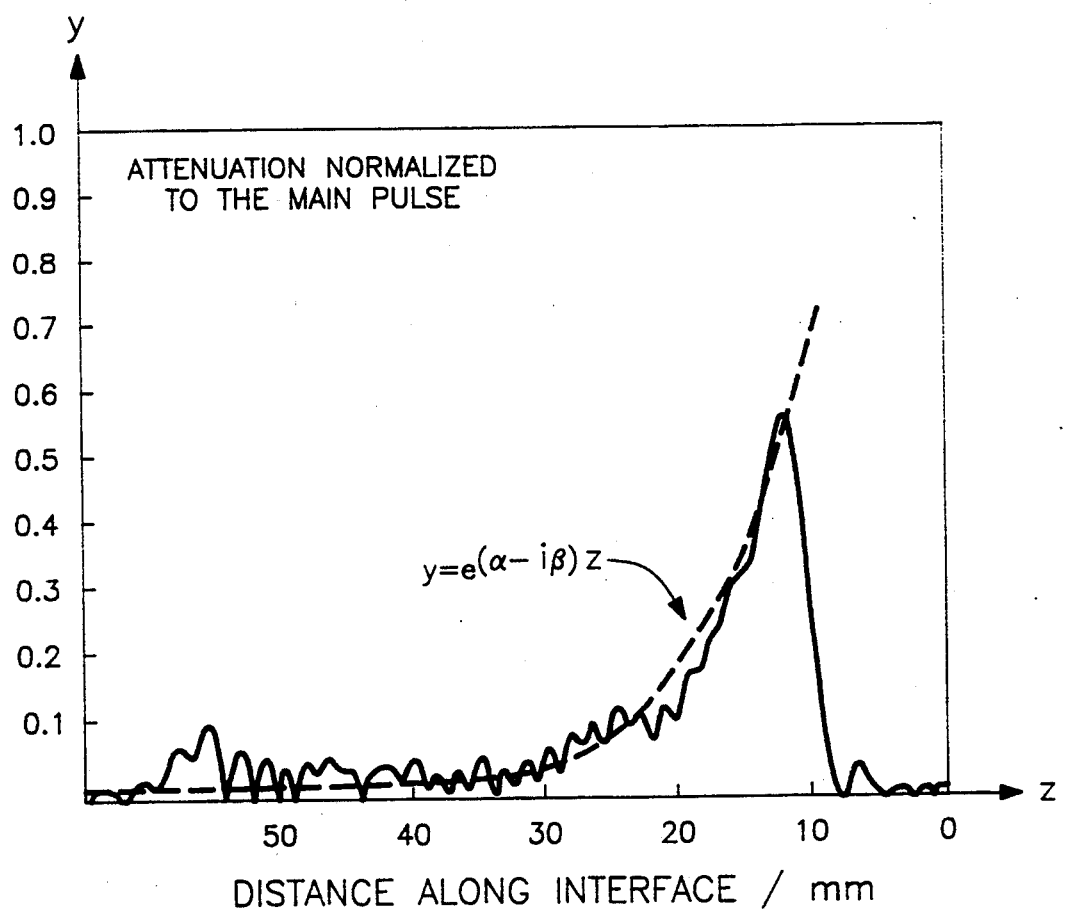
FIG. 14 is a graph showing the results of the attenuation measurements of the attenuation pattern shown in FIG. 13.

A schematic presentation of the expected acoustic energy, or attenuation pattern, is shown in FIG. 13. The thick arrow 52 indicates the direction of the acoustic energy flow while the interface wave propagates along the interface. The energy flow direction (Poynting vector) is shown by arrows 54 and is not parallel to the direction of propagation. This is characteristic of the interface waves. The measured attenuation of the mode as a function of interface length is shown in FIG. 14. The attenuation normalized to the main pulse, is plotted as a function of distance. The pronounced maximum of the leaking energy measured at the surface of cladding (located at the 10th mm) is connected to an angle of maximal energy flow and causes the characteristic "lacuna" in the receiving pattern. The same leaky mode was detected after interchanging the position of the transmitter and receiver. There is a pronounced maximum of the leaking energy measured at the surface of cladding along the direction parallel to the interface. This maximum is connected with the angle of maximal energy flow associated with the direction of the Poynting vector. After this point, the energy attenuates as the square of the displacement attenuation. A characteristic "lacuna" can be expected after startup of a leaky wave. Even at high frequencies, when the imaginary part of the higher modes in a family is quite small, the leakage angle for a mode can be finite and large if the wave speeds in the rod are larger than those in the matrix (cladding). Because of the interference pattern near the interface between longitudinal and shear type components, the energy flow bends and, therefore, the edge of the lacuna shifts from the position estimated from the asymptotic leakage angle of the mode. This shift, analogous to the Goos-Hänchen shift in optics (see F. Goos and H. Hänchen, Ann. Phys. 1, 333–346 (1947); F. Goos and H. Hänchen, Ann. Phys. 5, 251–2XX (1949)) and the Schoch effect in acoustics (see A. Schoch, Acustica 2, 1–17 (1952)), can be obtained directly by following the energy flow pattern discussed in detail above. In a cylindrical geometry there are an infinite number of interface leaky modes, but only a finite number in a planar interface geometry. The substance of the above publications is incorporated herein by reference.

The existence of faster modes with group velocity approaching the longitudinal velocity in aluminum is a consequence of the cylindrical geometry of the fiber interface. The phase velocities of these modes have been measured using interface wave acoustic microscopy.

Figure 15:
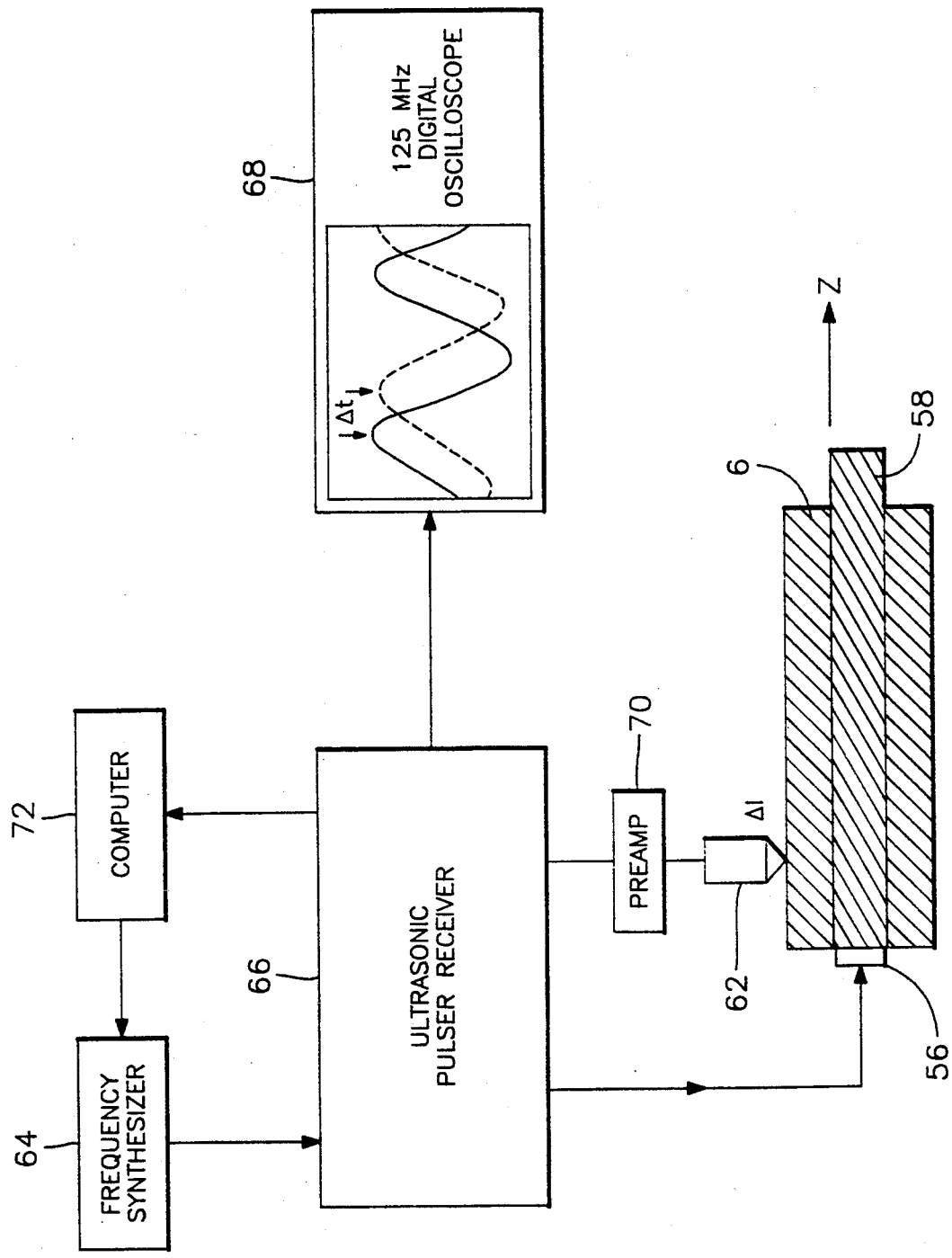
FIG. 15 is a flow diagram showing a prototype interface wave microscope.

A prototype of an interface wave microscope is indicated schematically in FIG. 15. A general outline of the measurement process is now given.

The sample of rod 58 in an aluminum cylinder matrix 60 containing the cylindrical interface was placed on the movable microscope table (not shown). The arrangement of the transmitter 56 is similar to that shown in FIG. 9. Next, the transducer (T) was used to excite the interface wave along the interface. A broadband "point" receiver transducer 62 was placed directly at the surface of the cladding. A frequency synthesizer 64 produces a signal inputted to ultrasonic pulse receiver 66. The chosen leaky mode was traced along the interface. At two arbitrary positions of the receiver, $x_1$, and $x_2$, the time difference, $t_1$, and $t_2$ was obtained by a pulse overlap technique. Knowing the distance $\Delta x$ and the difference $\Delta t$ in travel time from $x_1$ to $x_2$, the phase velocity of the interface wave for an arbitrary position on the interface was obtained. A more detailed analysis would reveal that the transmitting transducer generates a surface acoustic wave that converts into a radial-axial leaky mode at the interface. This mode radiates acoustic energy into the matrix when it travels along the interface. The receiver 62, a movable- conical transducer, used in this scanning system was placed directly against the outer aluminum surface of the sample. The phase velocities of the interface modes as a function of frequency for fixed diameter of the rod was measured. A silicone couplant was used to maintain uniform reproducible results. A narrowband pulse gated from the frequency synthesizer 64 was sent to the ultrasonic pulser receiver 66 which outputted a signal to ultrasonic transmitter 56. The receiving transducer 62 detected the signal and the waveform was fed to ultrasonic pulser receiver 66 which outputted a signal to be stored in the memory of the digital oscilloscope 68. After a small translation of the receiver, dx, the new waveform was compared with a previously stored one and the time difference, dx, between the two positions of the receiver was used for the phase velocity evaluation $v = dx/dt$. A preamplifier 70 was used with receiver 62 and computer 72 was connected between ultrasonic pulser receiver 66 and frequency synthesizer 64.

Figure 16:
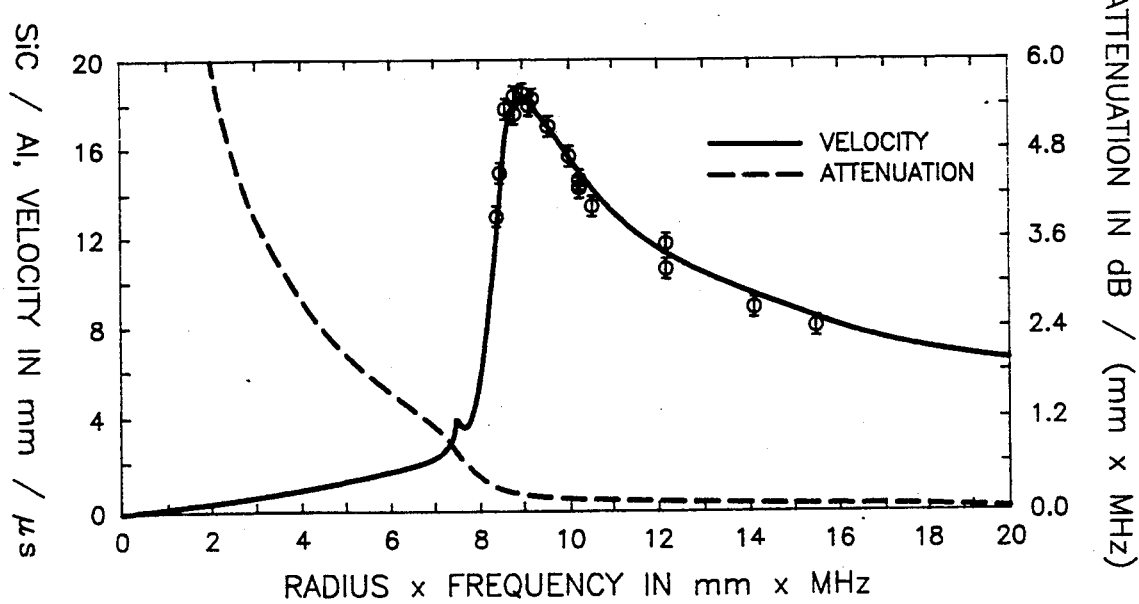
FIG. 16 is a graph showing a comparison between the calculated dispersion curve and measured phase velocity as a function of the dispersion parameter and the calculated attenuation for the example of FIG. 15.

This technique compares two sinusoidal waveforms with respect to a maximum or minimum of the wave amplitude and measures the phase velocity of the traveling interface wave if the receiving pulse does not differ significantly from the stored reference. This technique is most effective if the transmitting pulse has a narrow bandwidth. FIG. 16 shows the comparison between the experiment and the theory. The calculated dispersion curve (continuous line), and the imaginary part, which determines the attenuation (dotted line), is compared with the measured phase velocity (points) as a function of the dispersion parameter (frequency x radius) for one of the Al—SiC interface modes. The dotted line shows the calculated attenuation for this leaky, radial-axial mode at the Al— SiC interface. We see that there is a very good agreement of the measured and calculated phase velocities, and that the measured velocity of this interface wave is high, larger than 19 km/s. The very good agreement between the theory, based on the assumption of the elasticity of both materials, and the experimental data taken for the different frequencies, confirms the validity of the assumption of well bonded interfaces between two elastic solids.

Figure 17:
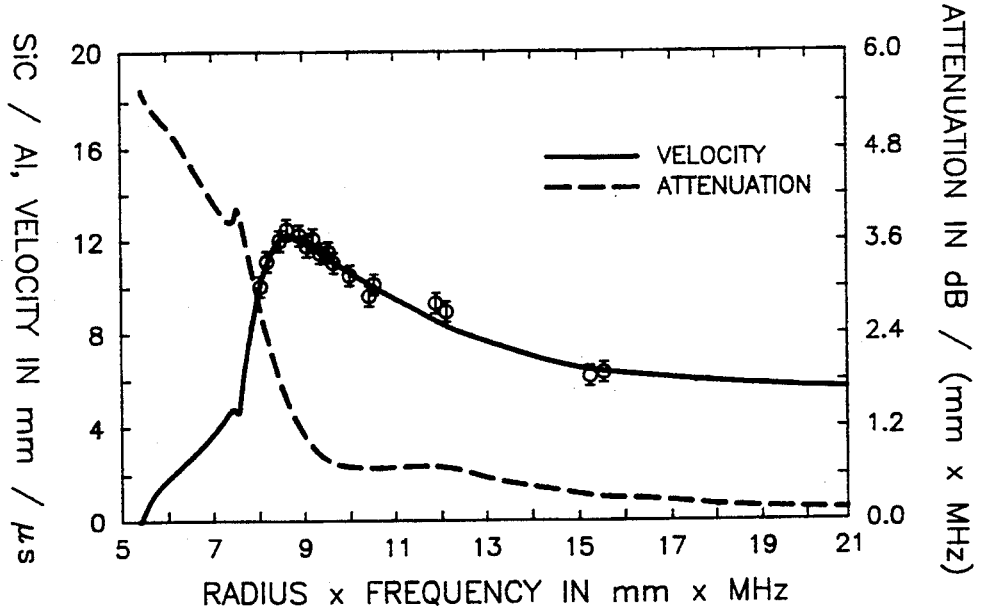
FIG. 17 is similar to FIG. 16 and shows a comparison for another radial-axial leaky mode at the aluminum-silicon carbide interface.

FIG. 17 shows the dispersion relations calculated and measured for another interface radial-axial mode propagating at an aluminum-silicon carbide interface. The dotted line shows calculated attenuation (imaginary part of the velocity) for this mode. The experimental points were obtained for a fixed diameter of the rod as a function of frequency. Because each mode is a harmonic wave, each particle of the medium traces out an elliptical trajectory in the (r,z) plane. Graphical representations of particle motion have been developed, allowing visualization of the interaction of each radial-axial mode with the interface. In addition, the time-averaged Poynting vector, the generalized group velocity, the energy flow curve, and the attenuation along the interface have been calculated to allow a comparison with experiments. For leaky modes, the displacement amplitude falls off exponentially along the Z direction while the Poynting vector components and energy density drop off as the square of the amplitude. By contrast, the group velocity is independent of z and depends only on radius. Because of this independence of z, energy leaking away from the interface (far enough from the interface) follows parallel curves. Far from the interface these waves have a natural propagation direction along a cone which is traced out by the energy velocity field, and they exponentially decay in a direction perpendicular to this direction.

The radial-axial modes in an infinitely clad isotropic rod have been studied in detail and it has been shown that in metal matrix composites, where the fibers are stiffer than the matrix, many of these modes are leaky, transmitting energy into the surrounding medium.

Aluminum-Steel Interfaces, Shallow Angle Modes

Table I lists the calculated velocities for two weakly attenuated radial-axial modes in aluminum-steel. The following measured values were taken for calculations: density of aluminum $\rho_c = 2.77$ g/mm$^3$; longitudinal velocity of Al, $a_c = 6.323$ [mm/$\mu$s]; shear velocity of Al, $b_c = 3.10$ [mm/$\mu$s], density of steel, $\rho R = 7.99$ g/mm$^3$, longitudinal velocity of steel, $a_R = 5.92$ [m/$\mu$s], shear velocity of steel, $b_R = 3.25$ [mm/$\mu$s].

TABLE I

Table I. Calculated attenuation and phase velocities for two weakly leaking radial-axial modes in aluminum-steel. At 15 MHz these two modes propagate along the interface with the same phase velocity 3.1 mm/$\mu$s.

| | Mode 1 | | Mode 2 | |
|---|---|---|---|---|
| F MHz | V mm/$\mu$s | $\alpha$ dB/mm | $V^a$ mm/$\mu$s | $\alpha$ dB/mm |
| 1 | 4.7325 | 2.237 | 0.0127 | 272.134 |
| 2 | 3.6218 | 0.9874 | 0.02563 | 271.122 |
| 5 | 3.2043 | 0.36567 | 0.0655 | 263.87 |
| 10 | 3.1809 | 0.5369 | 2.456 | 220.1641 |
| 15 | 3.1803 | 0.7305 | 3.1800 | 100.00 |
| 20 | 3.1799 | 1.0352 | 6.2687 | 11.058 |
| 50 | 3.1809 | 2.573 | 3.4630 | 0.30235 |
| 100 | 3.1814 | 5.1397 | 3.298 | 0.09604 |

V = phase velocity of interface wave.

Figure 18:
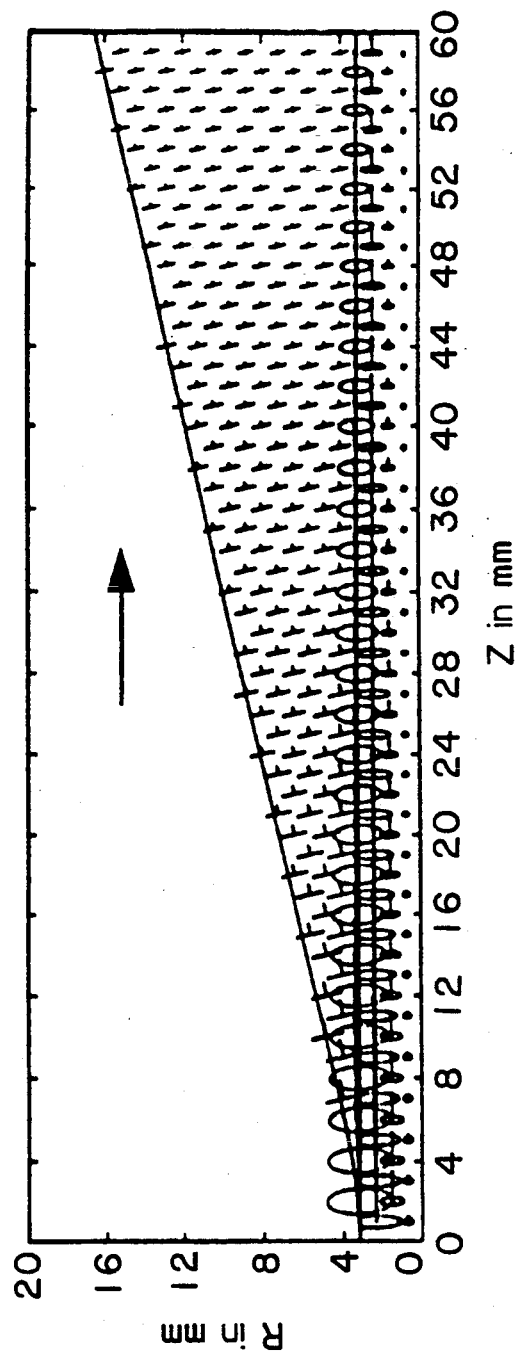
FIG. 18 is a graph showing the displacement field of a weakly leaking radial-axial mode calculated for the cylindrical interface between the aluminum matrix and steel rod for the sample shown in FIG. 1.

The displacement field of the weakly leaking radial displacement mode is shown in FIG. 18. The length of the interface along the z axis is 60 mm, the radius of the rod is 3.2 mm, and the outer radius of the aluminum matrix is 25 mm. The calculations were done for the sample geometry shown in FIG. 1. The elliptical particle trajectories in FIG. 18 show the relative amplitudes of the Z (horizontal) and R (vertical) displacement components at points uniformly distributed in the sample. The direction of energy flow, the Poynting vector, is depicted by the arrow stemming from the center of each ellipse. The length of the arrows corresponds to the relative magnitude of the Poynting vector. This figure also shows the decay of the wave amplitude. The continuous thick lines show the energy path of a wave packet starting at the edge of the interface found by integrating the Poynting vector. For Stoneley type and other nonattenuating waves (for example, Love waves), the Poynting vector is parallel to the interface. For leaky waves, this nonzero characteristic angle of leakage depends on the imaginary part of the velocity and on the attenuation. The angle is, in fact, determined as that which balances the exponential growth in the R direction with the exponential decay in the Z direction.

Figure 19:
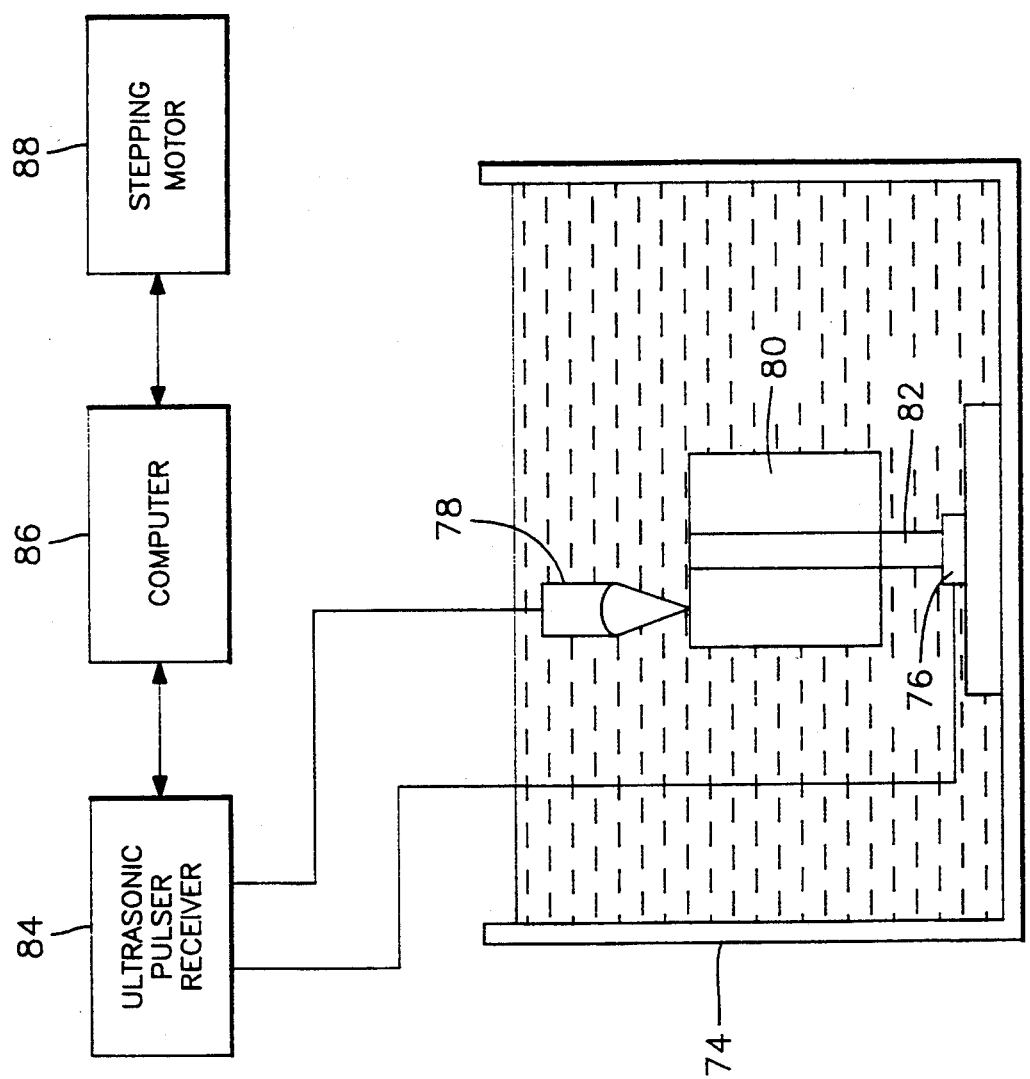
FIG. 19 is a schematic view of the transmitter and receiver in an acoustic microscope experiment.

For cylindrical geometry, the attenuation as well as the characteristic angle of leakage are frequency dependent. Although both are observed to increase with increasing wavelength at constant R, this is not generally the case. Exact measurements of the angle of the Poynting vector are affected by the shift in energy flow in the matrix close to the interface. Rays close to the interface do not travel in straight lines. It is of a different nature than the Goos-Hänchen shift, observed for a bounded beam at optical interfaces in the vicinity of the critical angle of a reflected beam. Here, the observed changes in energy flow due to curvature are frequency dependent and are larger at lower frequencies. As seen from FIG. 18 this shallow angle mode cannot be detected at the surface of the sample shown in FIG. 1 because the cladding is too thick, or the length of the interface is too short. Thus, these measurements were carried out at the end of the Al-steel sample on the face perpendicular to the interface. The sample 80 similar to that of FIG. 1 was immersed in an acoustic microscope tank 74 of water, as shown in the schematic arrangement of the transmitter 76 and receiver 7B in FIG. 19. A 5-MHz lithium niobate X cut 41-deg transducer was used as transmitter 76. The transducer was attached to the steel rod 82 and used to excite rod modes, which in turn convert to interface waves. A 15-MHz acoustic microscope lens was used as receiver 78. The lens was focused at the surface perpendicular to the z axis (axis of rod 82), as shown in FIG. 19. The ultrasonic pulser receiver 84, computer 86, and stepping motor 88 are used similarly to that shown in FIG. 11.

Figure 20:
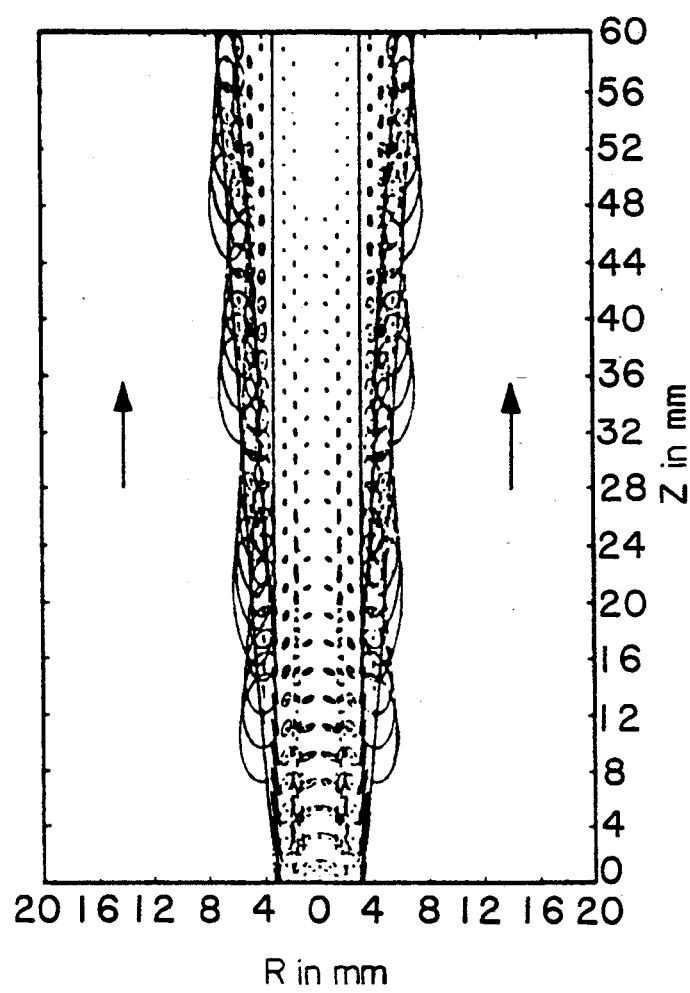
FIG. 20 is a view similar to FIG. 18 showing a full graphic illustration of the displacement field for the experiment shown in FIG. 19.
Figure 21:
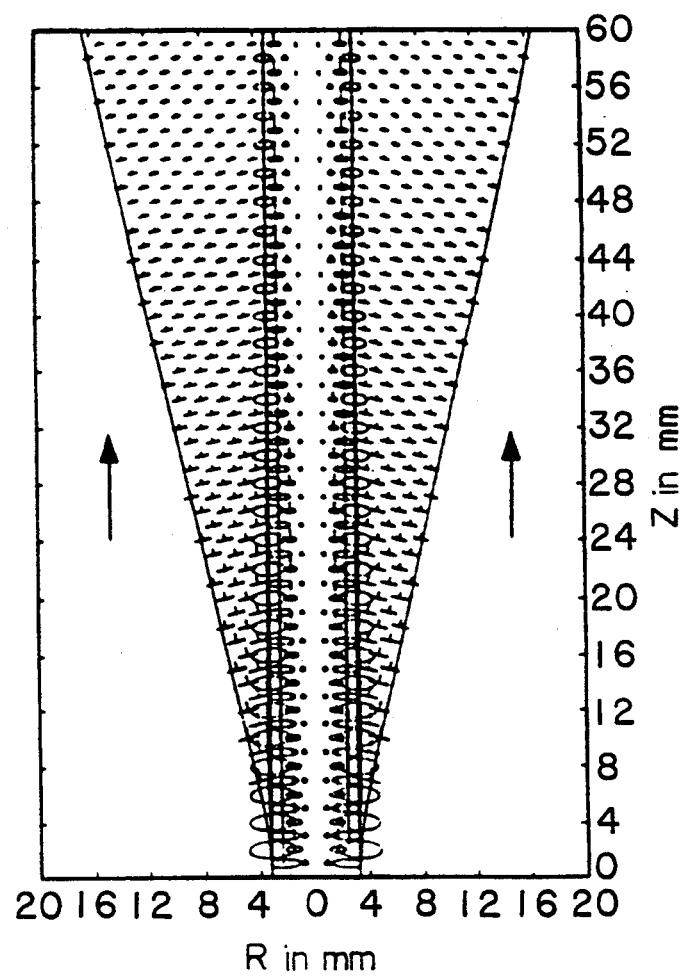
FIG. 21 is similar to FIG. 20 but shows a further view of the displacement field.
Figure 22:
FIG. 22 shows the imaged displacement field produced by the acoustic microscope in the experiment of FIG. 19 as shown on the computer display unit.
Figure 23:
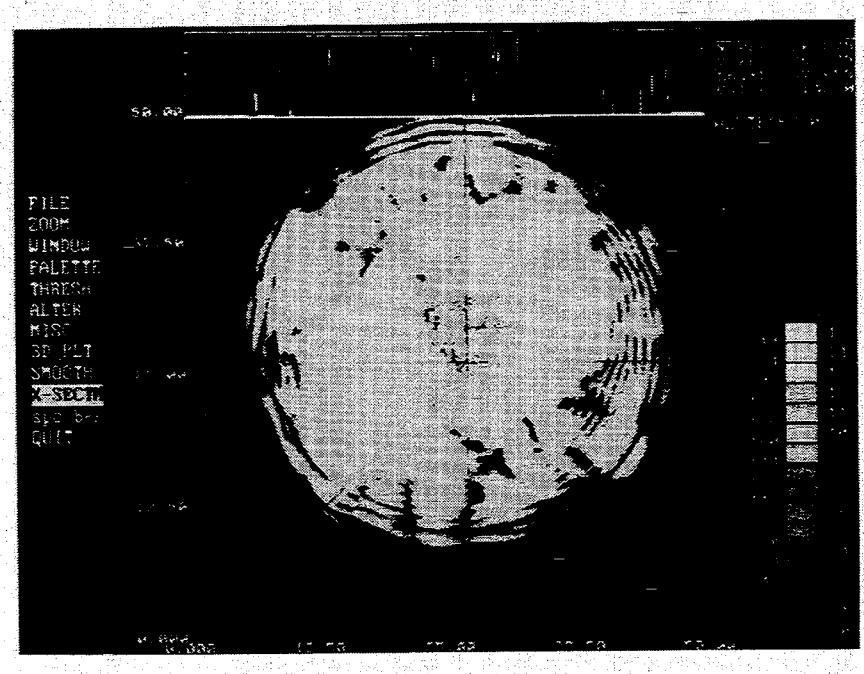
FIG. 23 is a magnified section of the image shown in FIG. 22.

FIG. 20 is a calculation, or computer simulation, of the displacement field of the leaky mode 2 of Table 1 for the Al-St sample of FIG. 1. FIG. 21 is the same as FIG. 20 for leaky mode 1 of Table I. The displacement field was imaged at this surface and the results are shown in FIG. 22 which shows the displacement field created by the two shallow angle modes listed in Table I. At 15 MHz these two modes have identical phase velocity, so it is impossible to separate them at this frequency by simple windowing. However, changing the frequency of the receiver to 10 MHz causes the complete disappearance of the slower mode (see Table I). FIG. 23 shows a magnification of the acoustic image from FIG. 22. In the upper part of this image the cross section presents the incident wave displacement field at the surface of the cladding.

Silicon-Carbide-Aluminum and Silico-Carbide-Copper Interfaces

The characteristic angle of leakage as a function of frequency was calculated for the four families of the SiC—Al modes. In general, with increasing frequency, the ratio of the ultrasonic wavelength to the radius of the rod changes; the leakage angle becomes more shallow until it reaches the constant value characteristic of the planar interface.

Figure 24:
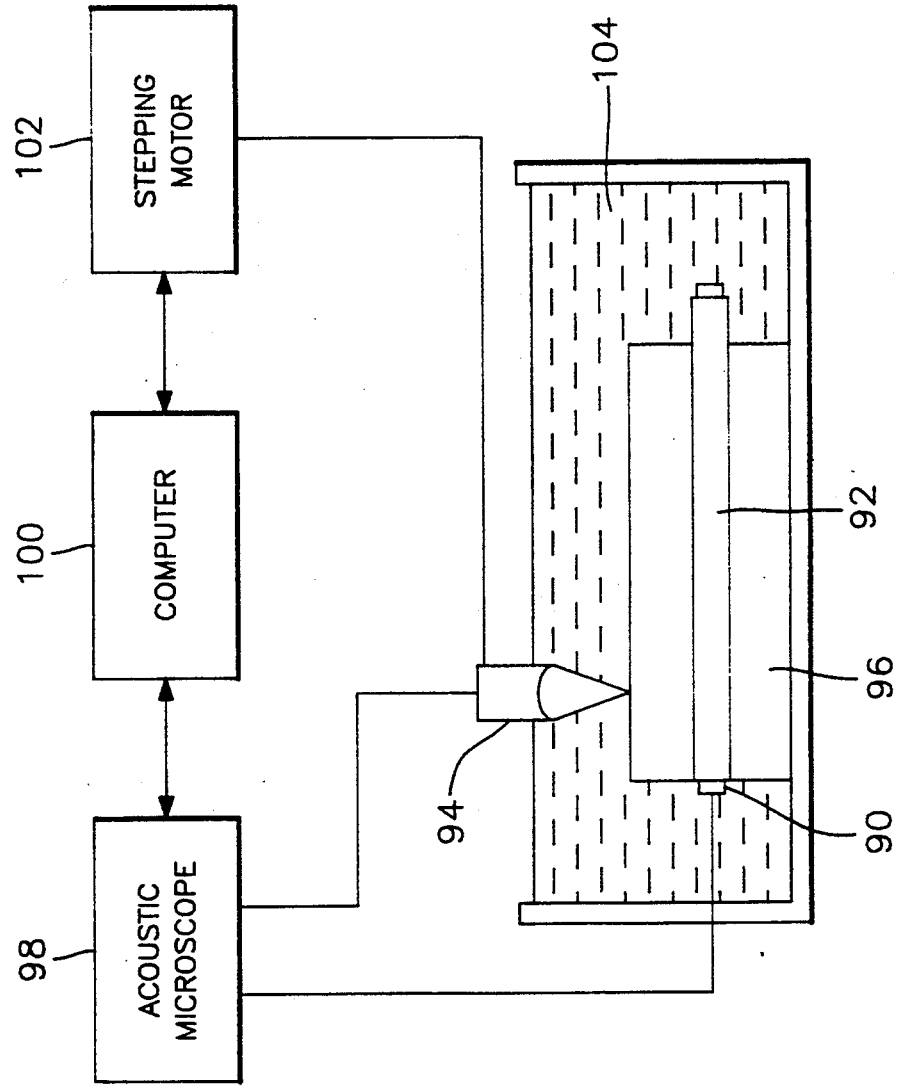
FIG. 24 is a schematic view of an arrangement of the acoustic microscope for another experiment with a SiC rod.

In this experiment we used the acoustic lens focused on the surface of aluminum matrix to receive the acoustic signals generated by the leakage from the displacement field. The schematic arrangement of the transmitter and the receiver is shown in FIG. 24 and is similar to that of FIG. 11. If the surface of the cladding is rough or damaged, the displacement field will be distorted and the signal coming from the interface will be affected. When the surface of the cladding is smooth the acoustic image will show no distortion. The acoustic microscope is schematically presented in FIG. 24 which shows the transmitter 90 attached to the end of rod 92 and movable receiver 94 focused at the surface of the Al matrix 96 of the sample immersed in water tank 104, the acoustic microscope 98, computer 100 and stepping motors 102. The acoustic lens 94 scans the acoustic arrival from the interface. This system was used to image the discontinuity of the materials at the interface.

Figure 25:
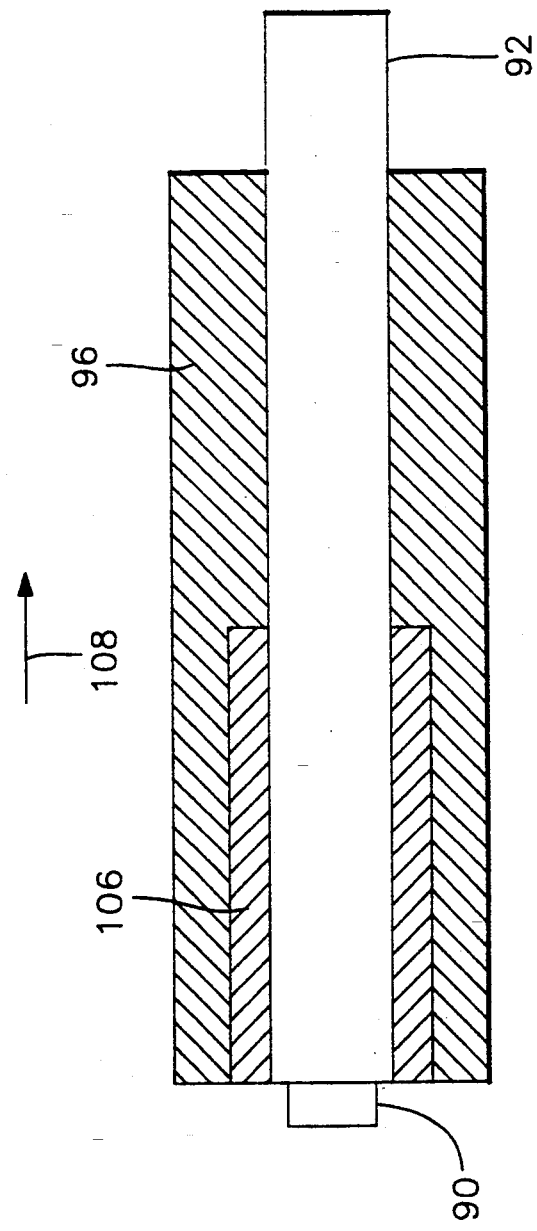
FIG. 25 is a cross-sectional view of the sample used in the experiment of FIG. 24.
Figure 26:
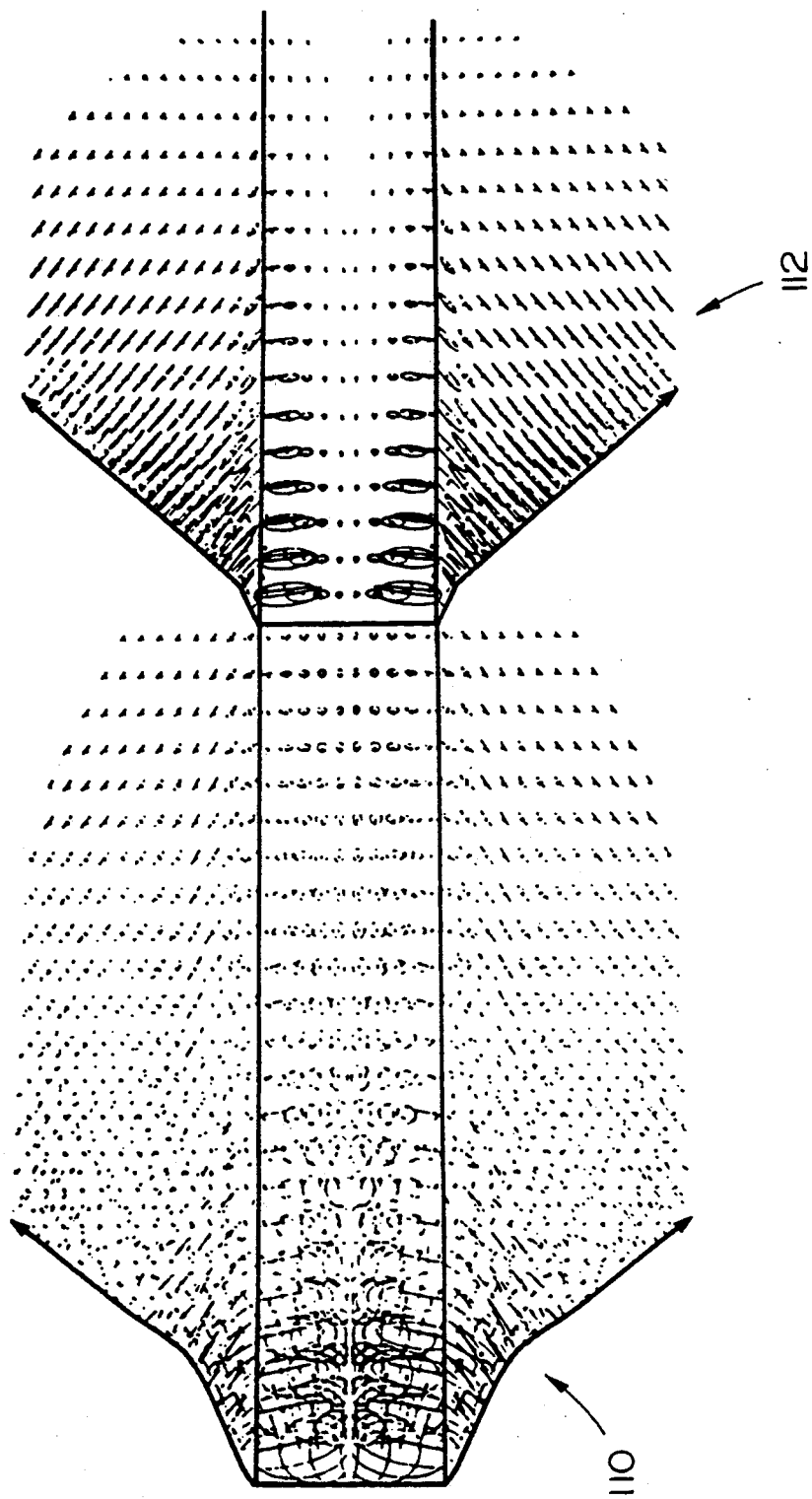
FIG. 26 shows schematically the calculated displacement field for the two modes produced in the sample of FIG. 25.
Figure 27:
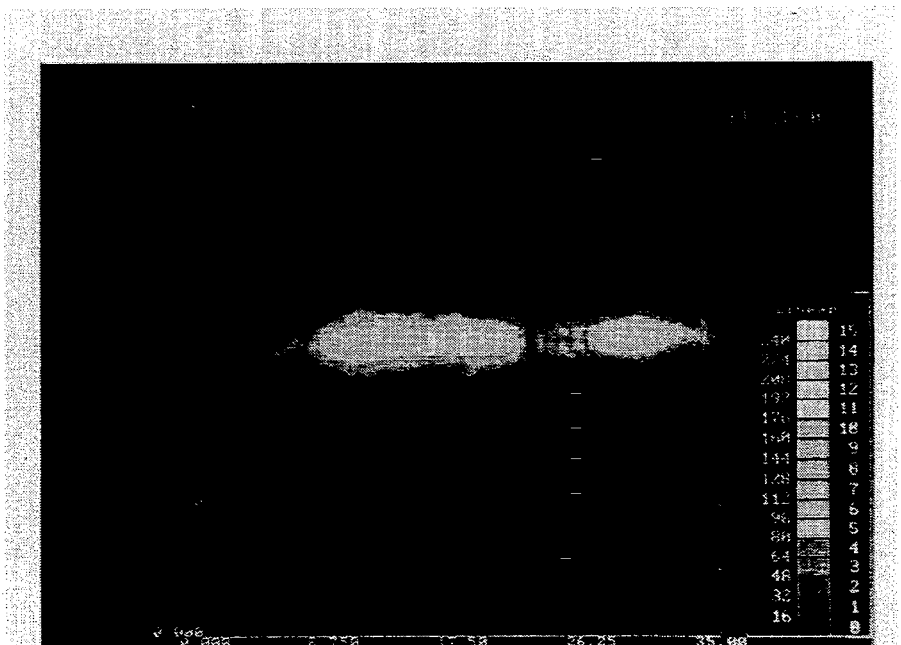
FIG. 27 shows an acoustic image of energy leaking from the interfaces of the sample of FIG. 25 as shown on the computer display unit.

The sample prepared by hot isostatic pressing contains the aluminum-silicon carbide interface, and in addition, the second half of the SiC rod was wrapped in a 3 mm thick layer of copper 106 before the sample was hot pressed in alumium and is shown in FIG. 25. The rod has a diameter of 6.13 mm and length of 58.35 mm and the AL cladding has an outer diameter of 17.26 mm, and a length of 50 mm. The interface wave that propagates on the SiC—Al interface reflects from the discontinuity, and part of the energy converts into a Cu—SiC interface mode. The calculated displacement field for these two modes is shown in FIG. 26. The arrow 108 in FIG. 25 points in the direction of propagation of the interface wave. The Cu—SiC mode 110 (FIG. 26) propagates forward, but part of the energy reflects from the Cu edge and another part converts into the Al—SiC interface mode. This new mode is at first characterized by a lacuna, the dark separation in the middle of the sample due to the leakage angle as shown in FIG. 27 which is an acoustic image of the type shown in FIG. 22, but for the experiment of FIG. 24. This mode bounces back and forth at the Cu—SiC interface, and has lower attenuation than Al—SiC mode 112 shown at the right-hand side of the image.

The acoustic image of the energy leaking from Al—SiC and Cu—SiC interfaces is shown in FIG. 27. There is good agreement between the calculated displacement field and the acoustic microscope image obtained at the surface of the cladding.

Figure 28:
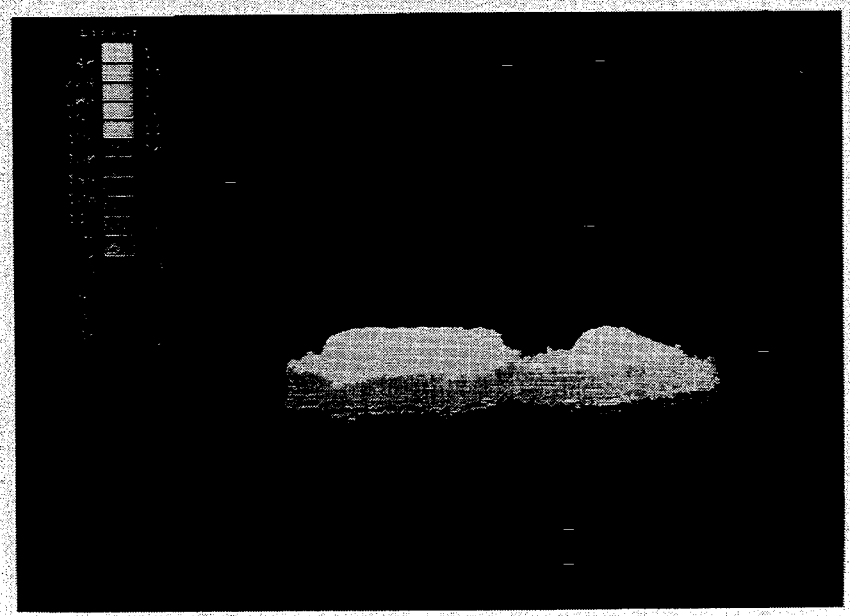
FIG. 28 shows the same image in FIG. 27 plotted as a function of the intensity of the leaking acoustic energy and is called 3-D acoustic image.

FIG. 28 shows the image of the displacement field created at the surface of the cladding by the two interface modes from the Al—SiC interface and the Cu—SiC interface as a function of the intensity of the acoustic energy.

Application of Interface Modes to Imaging Interfaces Between Two Solids

The traditional acoustic microscope approach to cylindrical interface testing employs one acoustic microscope lens working in an echo mode. However, the incident acoustic energy will be scattered by the cylindrical shape of the rod inside the cladding and the efficiency of this technique is low. Often, when the cladding material has a high acoustic impedance, it is necessary to use a special lens design in order to reach the interface.

The best images of the cylindrical interfaces are obtained when the transmitter and the receiver are moved simultaneously, while scanning the sample.

Examples of acoustic images, shown on the display unit of the computer in the acoustic microscope system, of cylindrical interfaces obtained with an experimental setup in accordance with the invention will now be described. The imaging process is illustrated schematically in FIG. 29 and consists of moving the transmitter 114 simultaneously with the receiver 116 over the metal cladding 3. The longitudinal wave sent through the water 120 at the optimum angle then converts into the desired interface mode. The leakage energy of this mode is detected by the receiver, consisting of the acoustic lens 116 focused at the surface of the cladding so that the focal point is at 118 for example.

Figure 29:
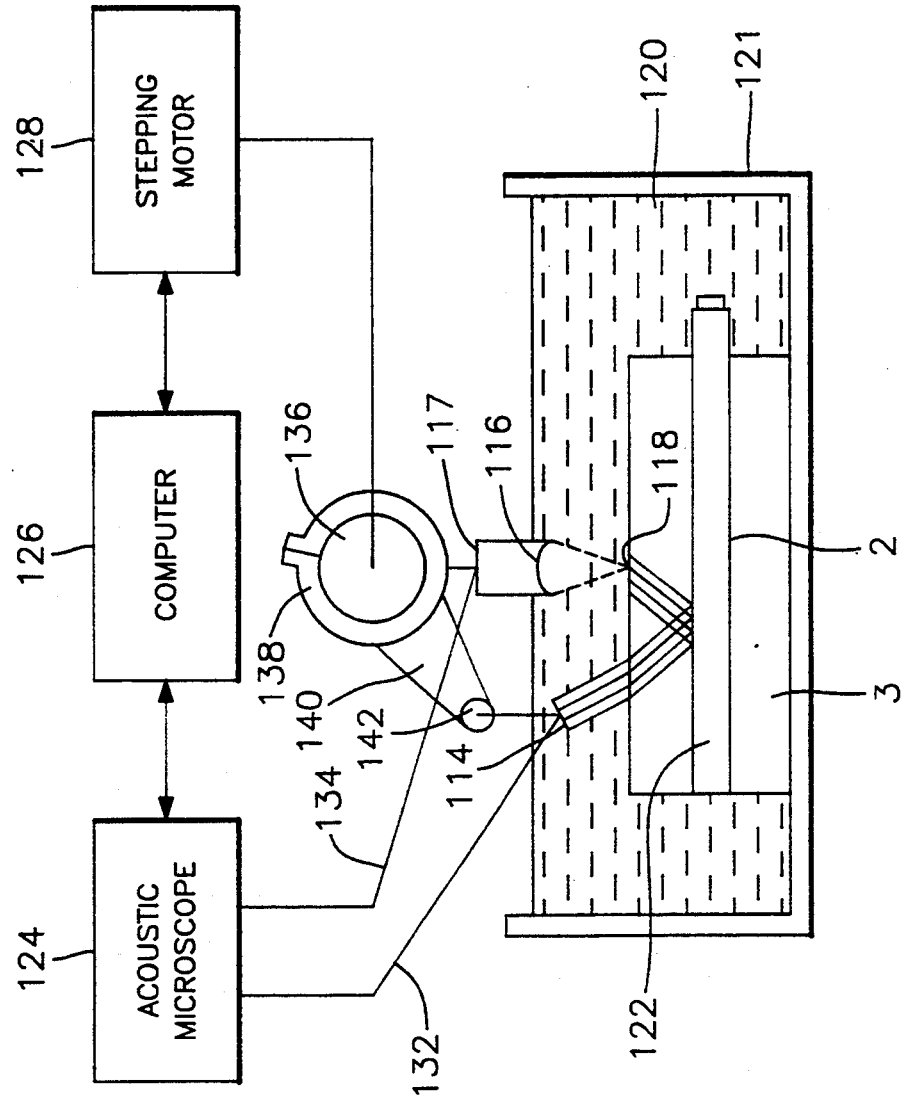
FIG. 29 is a schematic view showing an acoustic microscope system for imaging metal-interfaces in accordance with the invention.

In the application shown in FIG. 29, a 10-Mhz acoustic microscope lens 116, focused on the surface of the aluminum matrix 3, at focal point 118, was used as a receiver. The transmitter 114 consists of a planar, longitudinal transducer sending the energy directly to the interface 122. An additional refraction angle ϵ between water and cladding, must be considered in this application. FIG. 29 shows the schematics of that design. Transmitter 114 is connected to the acoustic microscope 124 by electrical conductor 132 and lens 116 is connected to the acoustic microscope by electrical conductor 134. A mounting shaft 136 is mechanically connected to the stepping motor device 128 so that it is moved relatively to the tank 121 and object being examined which is submerged in the water 120. Acoustic lens 116 is held in a support 117 which is connected to and supported on shaft 136. A clamping element, such as an adjustable C-clamp, 138 is rotatably mounted on shaft 136 and has an arm 140 extending outwardly therefrom. The outer end of arm 140 has a pivotable member 142 thereon for supporting transmitter 114 so that the angle of the transmitter and the acoustic waves emitted therefrom can be varied relative to the body being examined and the interface 122 therein. Arm 140 provides for adjustment of the distance between transmitter 114 and receiver 116 by rotation of clamping member 138, which is clamped tightly onto the shaft 136 after the predetermined distance between these two elements has been set. The structural details of the clamping ring 138 and pivotable support member 142 have not been shown since this would be readily understandable to one having ordinary skill in the art.

Figure 30:
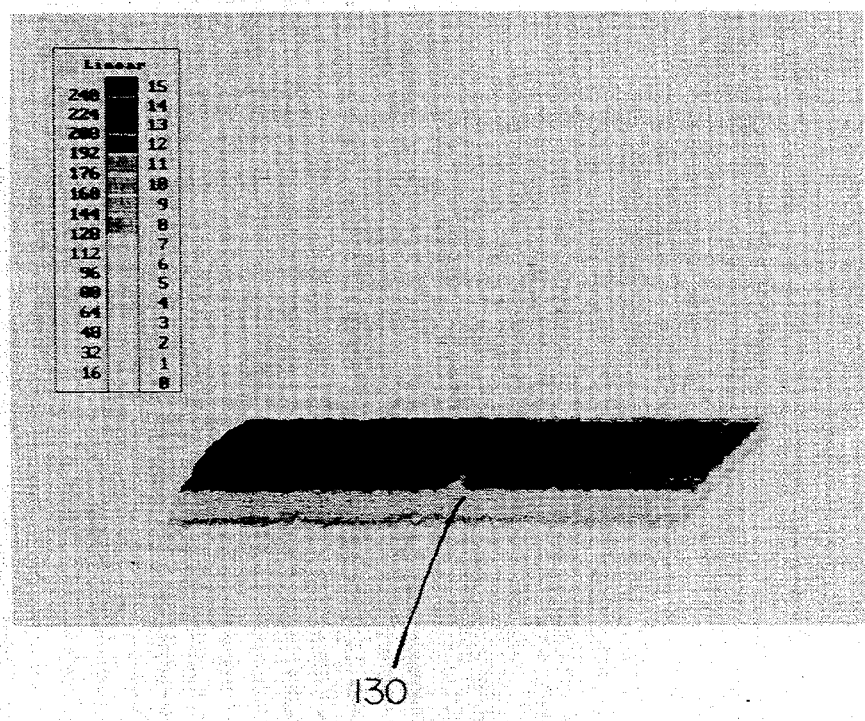
FIG. 30 is an acoustic microscope image, as shown on the computer display unit of the acoustic microscope system of the invention, of the metal-metal cylindrical interface where the rod was marked by a groove before being fitted into the aluminum cladding.
Figure 31:
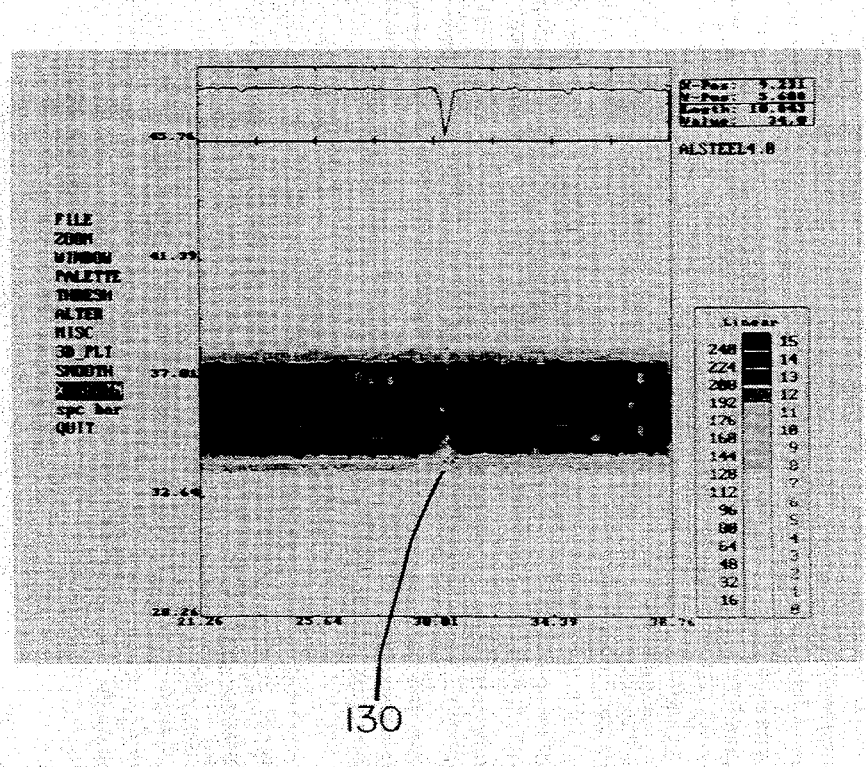
FIG. 31 is an enlarged image of the interface of FIG. 30 showing the defect (groove) in the middle of the lower surface of the rod.
Figure 37C:
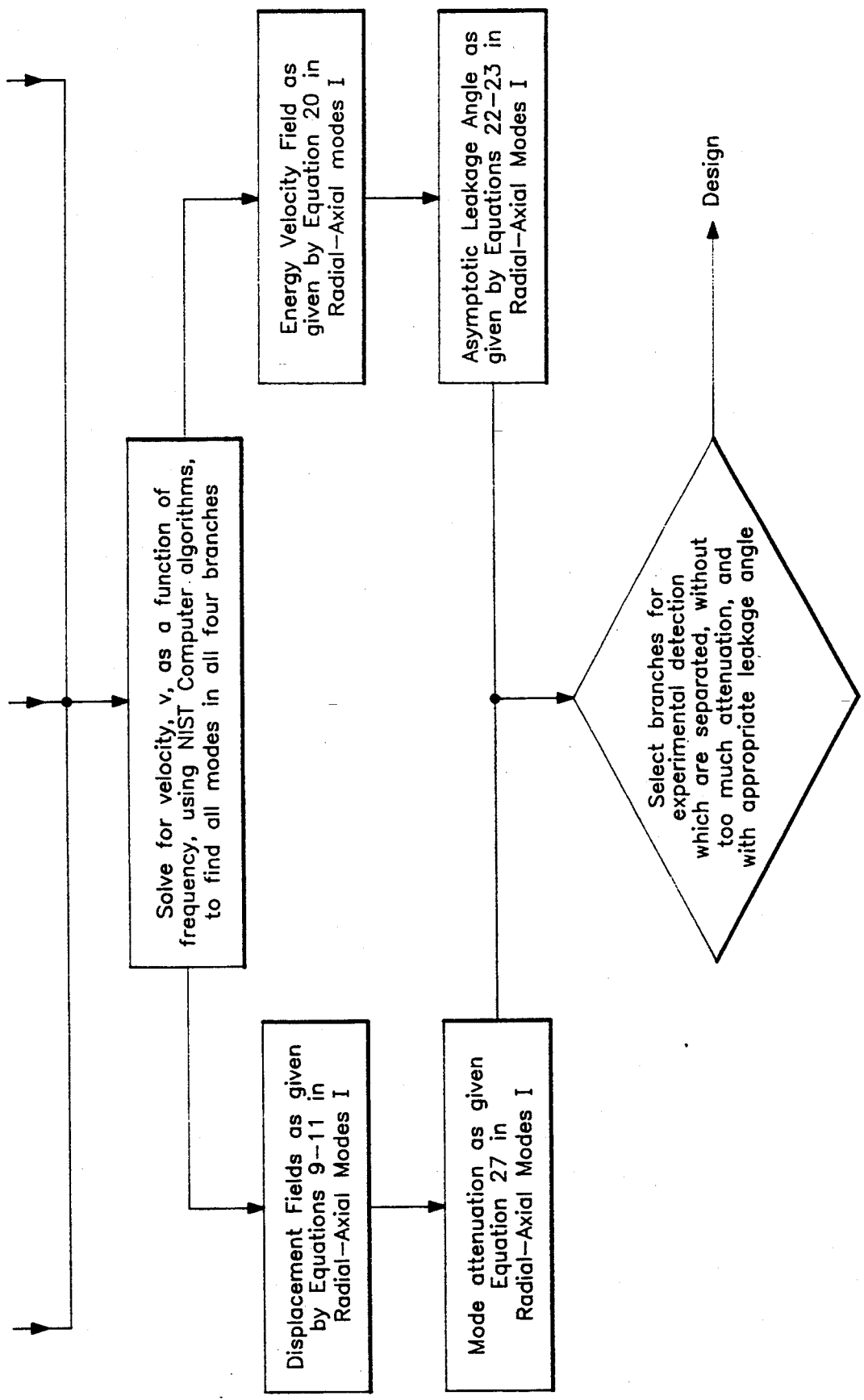

FIG. 30 shows an acoustic microscope image of the metal-metal cylindrical interface of the sample model of FIG. 1, where the rod 2 was marked on its lower surface by a groove before fitting it into the aluminum 3. The best images of the cylindrical interfaces were obtained by the invention wherein the transmitter and the receiver are moving simultaneously, illuminating the interface with the same intensity of the acoustic energy. In order to obtain the desired accuracy and resolution of the images of the interfaces inside of the cladding it is necessary to choose the correct interface mode which is determined in the manner shown in the flowchart of FIGS. 37(a) and 37(b). The size and shape of the groove defect are seen on the enlarged image of the interface at 130 in FIG. 30 and in the middle of the lower surface of the rod at 130 in FIG. 31. The cross-sectional image, generated by the image processing software, clearly reveals size and shape of the defect in the upper part of FIG. 31. Contrast in the above interface imaging is explained as follows: everywhere that the interface is well bonded, the guided wave can be propagated, and the receiver will monitor the acoustic energy of the leakage through the cladding. Under this condition, the interface will look much brighter than the background, as shown in FIG. 31. This image was obtained by using the low leakage angle aluminum steel interface mode.

Figure 36:
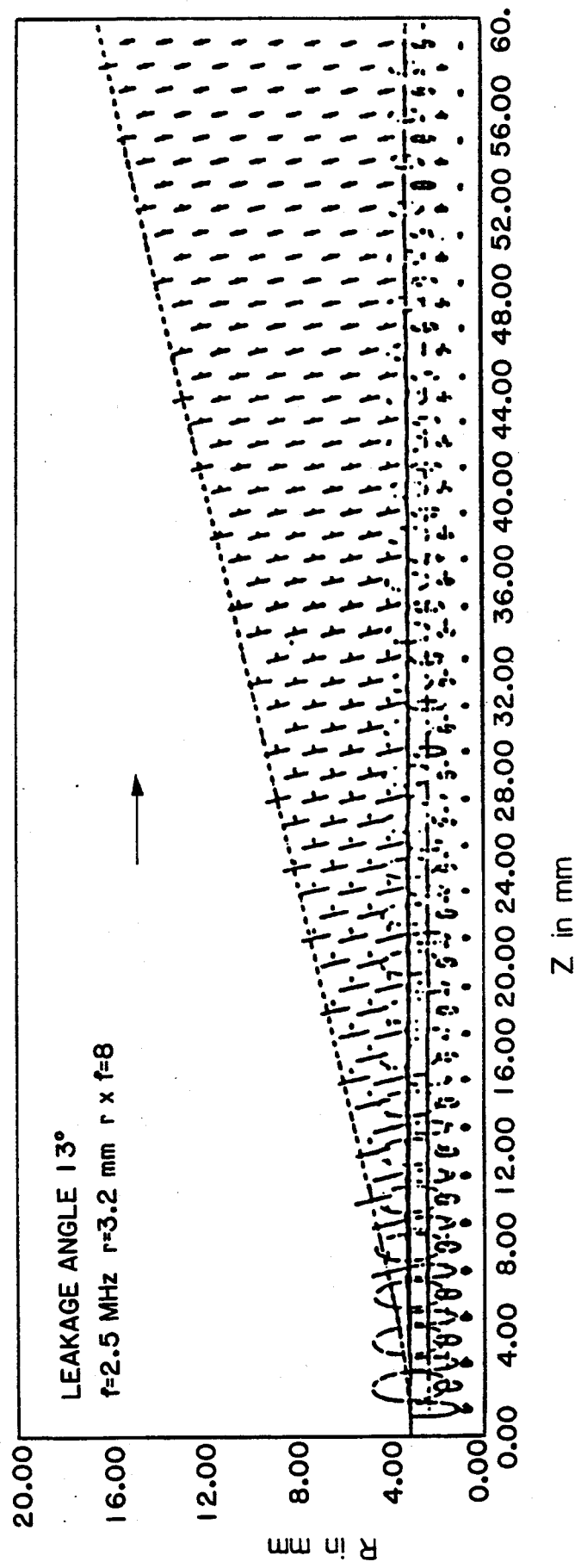
FIG. 36 is a computer simulated picture of the low leakage angle AL-ST interface mode in accordance with the invention.

The computer simulated picture of this mode propagating at the interface of interest is shown in FIG. 36. It is worth emphasizing that this particular mode is only slightly attenuated and the angle of leakage is shallow at 13°. The frequency f was 2.5 Mhz and r was 3.2 mm. This angle can be in the range of approximately 13° to 19°. Accordingly, $r \times f = 8$. The presented images are the examples in accordance with the invention of applications of the guided interface modes to acoustic microscopy of the interfaces between the two solid materials like metals or metal and ceramics. This is a nondestructive, non-invasive technique, but its successful application cannot be separated from the theoretical calculations of propagation and dispersion relations for every interface mode. Wherever the interface is unbonded, the guided leaky mode will convert into the two surface waves propagating along the two separated surfaces without loss. This example illustrates the feasibility of this technique for nondestructive examination of the interfaces such as weldings, adhesive bondings, and any other composite material containing bonded contacts between two solids. The miniature fibers will look as bright on acoustic microscope images as the model interfaces, assuming the frequency is scaled up appropriately. The diameters of the fibers in commonly used metal-matrix composites range from a few hundred to a few microns corresponding to a frequency range between 100 MHz and several GHz.

Figure 32:
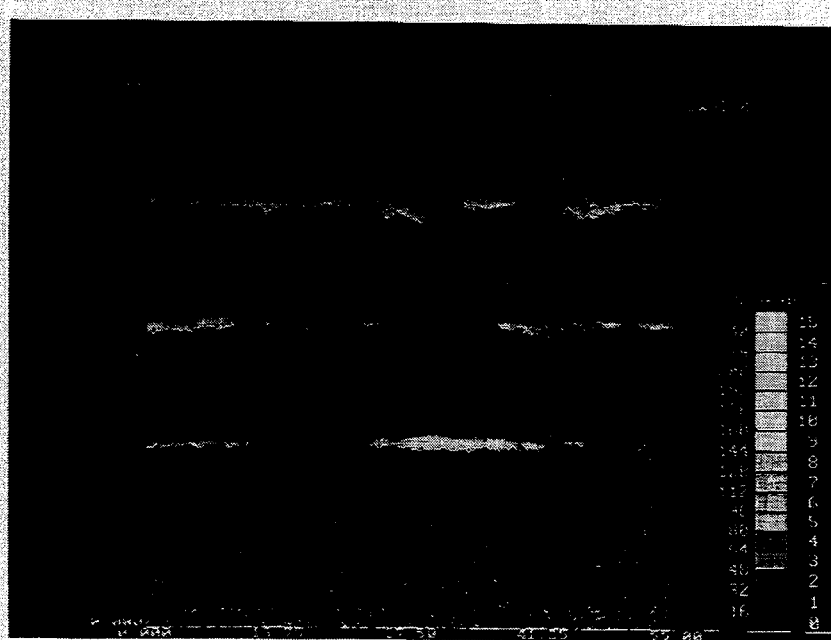
FIG. 32 is an acoustic microscope image of aluminum-steel interfaces created by casting in a mold obtained by using an interface wave designed lens.

FIG. 32 presents another practical industrial application of the invention. Using the guided wave lens design (separated transmitter and receiver) several acoustic microscope images were obtained of aluminum-steel cylindrical interfaces created by casting in a mold. The image is obtained by using interface wave designed lenses. This technique of making a well-bonded interface depends critically on the wetting properties of the molten metal. As can be seen in FIG. 32, the quality of the interfaces is poor.

Figure 33:
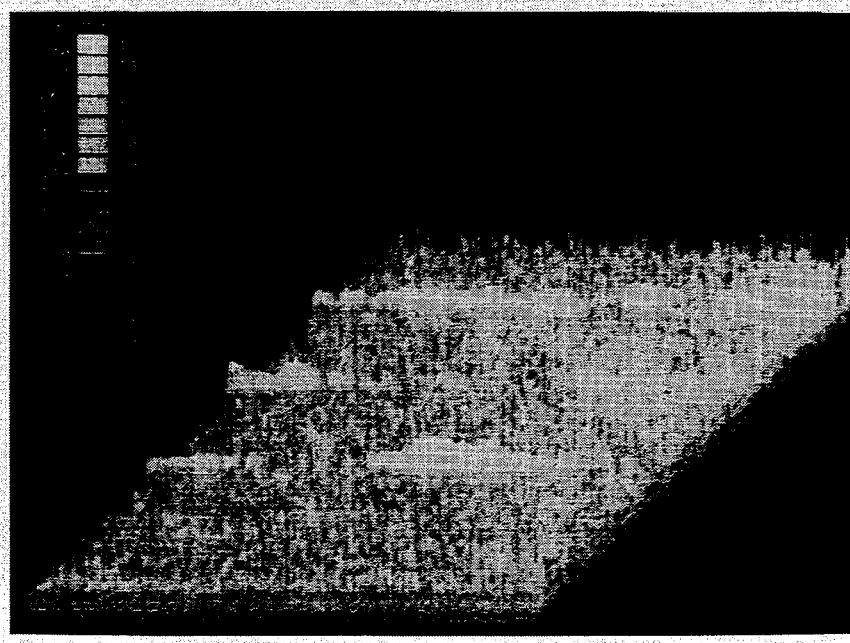
FIG. 33 is a magnified three-dimensional image of the section of the image shown in FIG. 32 and shows poor and irregular bonding where the surface of the interface is irregular.

The image shown in FIG. 33 is a magnified section of the image shown in FIG. 32 and presents the magnified image of a relatively better bonded interface. However, in this case one can inspect the surface of the interface inside the aluminum casting without damage to the interior of the sample. The interface wave can be propagated only at well bonded interfaces and the acoustic microscope image will show the bright surface of the interface. The three-dimensional image of FIG. 33 shows poor and irregular bonding where the surface of the interface is irregular.

If it is desired to obtain more-detailed information concerning the elastic properties, microstructure, porosity, or microcracks, or to detect the presence of the compounds growing between the two components of the interface, much higher frequencies are required in order to increase the resolution of the acoustic microscope images.

Figure 34:
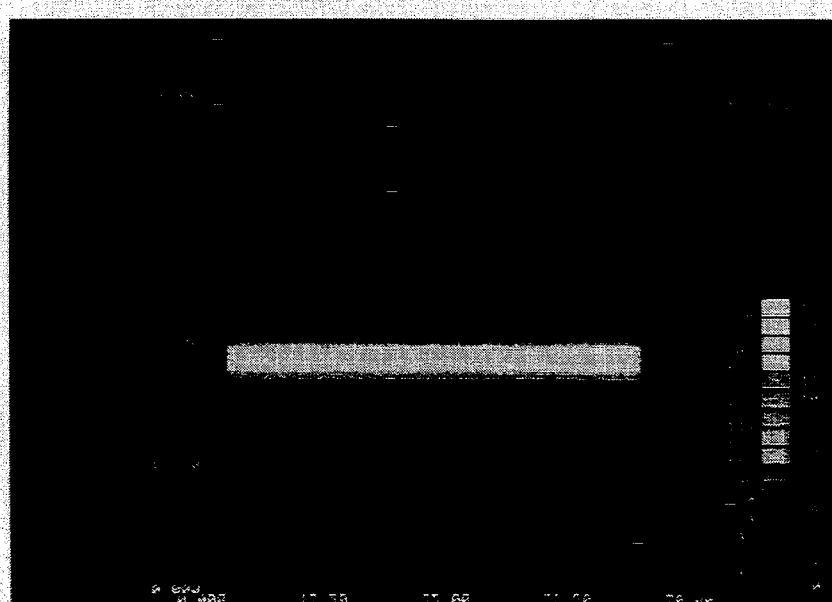
FIG. 34 is an acoustic microscope image of the interface between a steel rod and aluminum cladding.

FIG. 34 is an acoustic microscope image of the interface between a steel rod embedded in aluminum. Again, simultaneous translation of the transmitter and receiver was used to create the interface. This image was obtained for the sample shown in FIG. 1, and may be regarded as a spatial map of the interface wave interaction with the surface of the cylindrical interface. The interface in this case was a smooth and well-bonded metal-metal contact created by shrink fitting. The characteristic feature of the interface images obtained by the leaky wave technique is the brightness of the interface, in contrast with the images obtained by the echo technique.

Figure 35:
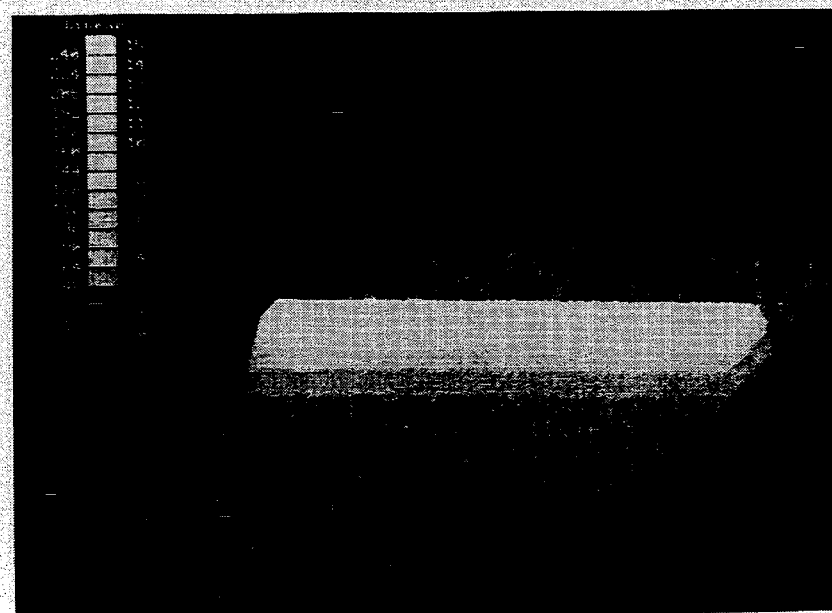
FIG. 35 is a three-dimensional image of the cylindrical interface shown in FIG. 34 plotted by 3-D software.

FIG. 35 shows the same image of the cylindrical aluminum-steel interface plotted in pseudo-3D form. The vertical, third dimension of FIG. 35 represents the intensity of the energy reradiated from the interface. No defects are observed at that interface. The bright picture of the surface of the cylindrical interface is an example of the enhanced resolution of the interfaces from the interior of solid materials.

FIG. 36 is similar to FIG. 18 and shows the displacement field of the weakly leaking radial displacement mode in accordance with the invention as schematically illustrated in FIG. 29 and wherein the frequency f equals 2.5 MHz, and the radius r of the rod is 3.2 mm so that r×f=8. The leakage angle is 13°. Where the sample is aluminum-silicon, the leakage angle is approximately 55°.

In investigating solid interfaces, existing acoustic microscope techniques suffer from a number of limitations. Conventional acoustic microscopy does, in fact, exploit leaky waves arising from solid-liquid interfaces, created when a broad angle lens is defocused below the surface of the solid material. Also, the b-scan technique takes advantage of the interference between liquid-solid leaky waves, and the signals rejected from the volume of the sample. However, a focused acoustic microscope lens has a continuous range of incidence angles, which can cause the excitation of a complicated mixture of interface guided modes at planar or cylindrical interfaces in bulk materials. The invention allows selectively exciting a single strong mode along the interface of interest, whereby direct information about the interface can be obtained.

As described above, the invention shows the feasibility of employing guided interface radial-axial modes in acoustic microscopy. The techniques of sending these waves along cylindrical interfaces have been described above and several direct applications to interface imaging are shown. These techniques are also valid for planar interfaces. The invention is not limited to the particular wavelength regime. The derived theory as well as the techniques discussed here for generating and detecting the interface waves on solid-solid interfaces can be applied over a range of frequencies extending from kHz to several GHz. The stored waveforms contain significant information about the physical and mechanical state of the two components creating the interface.

The application of guided waves to interface testing also allows one to obtain, in a noninvasive manner, the direct acoustic microscope images of interface properties from the interior of solid materials.

The foregoing description and accompanying drawings set forth the preferred embodiments of the invention at the present time. Various modifications, additions and alternative designs will, of course, become apparent to those skilled in the art in light of the foregoing teachings without departing from the spirit and scope of the disclosed invention. Therefore, it is to be understood that the invention is not limited to the disclosed embodiments but may be practiced within the full scope of the appended claims.

We claim:

1. An apparatus for non-destructive examination of at least one interface within a body between at least two separate elements of the body, comprising:
   an acoustic microscope comprising an ultrasonic transmitter for transmitting ultrasonic waves toward said body to be examined to produce an interface wave along said at least one interface, and an ultrasonic receiver for receiving acoustic leaking energy from said interface wave at said at least one interface;
   means for supporting said body; and
   means for supporting said ultrasonic transmitter and receiver in relative spaced relationship for simultaneous scanning movement with respect to said body at the same scanning speed so that said transmitter produces transmitted ultrasonic waves penetrating one of said elements of said body at a predetermined angle and propagating an interface wave along said at least one interface which radiates said acoustic leaking energy detectable by said receiver.

2. The apparatus as claimed in claim 1 and further comprising:
   means for adjustably mounting said transmitter on said transmitter and receiver supporting means so that said transmitted waves are directed at a predetermined transmitted angle relative to said at least one interface dependent upon the materials of said separate element of said body, and said acoustic leaking energy from said at least one interface is directed at a leakage angle relative to said at least one interface.

3. The apparatus as claimed in claim 1 wherein said body is solid and further comprising:
   a tank of liquid; and wherein
   said receiver includes a receiver lens;
   said means for supporting said body comprises means for holding said body immersed in said liquid; and
   said means for supporting said ultrasonic transmitter and receiver comprises means for supporting said ultrasonic transmitter and said receiver lens substantially immersed in said liquid.

4. The apparatus as claimed in claim 2 wherein said body is solid and further comprising:
   a tank of liquid; and wherein
   said receiver includes a receiver lens;
   said means for supporting said body comprises means for holding said body immersed in said liquid; and
   said means for supporting said ultrasonic transmitter and receiver comprises means for supporting said ultrasonic transmitter and said receiver lens substantially immersed in said liquid.

5. The apparatus as claimed in claim 2 wherein:
   said at least two separate elements comprise aluminum and steel;
   said transmitter directs said transmitted ultrasonic waves to pass through said aluminum prior to impinging on said at least one interface; and
   said transmitted angle is in a predetermined range so that said leakage angle is in the range of approximately 13° to 19°.

6. The apparatus as claimed in claim 2 wherein:
   said at least two separate elements comprise aluminum and silicon carbide;
   said transmitter directs said transmitted ultrasonic waves to pass through said aluminum prior to impinging on said at least one interface; and
   said transmitted angle is predetermined so that said leakage angle is approximately 55°.

7. The apparatus as claimed in claim 3 wherein:
   said at least two separate elements comprise aluminum and steel;

said transmitter directs said transmitted ultrasonic waves to pass through said aluminum prior to impinging on said at least one interface; and said transmitted angle is in a predetermined range so that said leakage angle is in the range of approximately 13° to 19°.

8. The apparatus as claimed in claim 4 wherein:

said at least two separate elements comprise aluminum and steel;

said transmitter directs said transmitted ultrasonic waves to pass through said aluminum prior to impinging on said at least one interface; and said transmitted angle is in a predetermined range so that said leakage angle is in the range of approximately 13° to 19°.

9. The apparatus as claimed in claim 3 wherein:

said at least two separate elements comprise aluminum and silicon carbide;

said transmitter directs said transmitted ultrasonic waves to pass through said aluminum prior to impinging on said at least one interface; and said transmitted angle is predetermined so that said leakage angle is approximately 55°.

10. The apparatus as claimed in claim 4 wherein:

said at least two separate elements comprise aluminum and silicon carbide;

said transmitter directs said transmitted ultrasonic waves to pass through said aluminum prior to impinging on said at least one interface; and said transmitted angle is predetermined so that said leakage angle is approximately 55°.

11. The apparatus as claimed in claim 1 and further comprising:

means for producing an image of said acoustic leaking energy received by said receiver.

12. The apparatus as claimed in claim 8 and further comprising:

means for producing an image of said acoustic leaking energy received by said receiver.

13. A method for non-destructive examination of at least one interface within a body between at least two separate elements of the body, comprising:

providing an acoustic microscope comprised of an ultrasonic transmitter and an ultrasonic receiver having a receiver lens;

supporting a body having at least one internal interface between said at least two separate elements therein;

supporting said ultrasonic transmitter in spaced relationship to said body;

exciting said ultrasonic transmitter to produce transmitted ultrasonic waves;

directing said transmitted waves at a predetermined angle toward said at least one interface within said body and producing at least one interface wave along said at least one interface;

positioning said ultrasonic receiver in spaced relationship with respect to said transmitter for receiving acoustic leaking energy from said at least one interface wave;

moving said transmitter and receiver simultaneously relatively to said body being examined at the same scanning speed so that said transmitted waves propagate said at least one interface wave along said at least one interface which radiates acoustic leaking energy from each point in said at least one interface; and receiving said acoustic leaking energy by said receiver.

14. The method as claimed in claim 13 and further comprising:

directing said transmitted waves at a predetermined angle relative to said interface depending upon the materials of said separate elements.

15. A method as claimed in claim 13 and further comprising:

focusing said receiver lens so that the focal point thereof is on the surface of said body.

16. The method as claimed in claim 14 wherein:

said at least two separate elements comprise aluminum and steel;

said transmitter directs said transmitted waves to pass through said aluminum prior to impinging on said at least one interface;

said acoustic leaking energy radiates at a leakage angle relative to said interface; and said predetermined angle is in a range so that said leakage angle is in the range of approximately 13° to 19°.

17. The method as claimed in claim 14 wherein: said at least two separate elements comprise aluminum and silicon carbide; said transmitter directs said transmitted waves to pass through said aluminum prior to impinging on said at least one interface;

said leaky acoustic leaking energy radiates waves radiate at a leakage angle relative to said interface; and said predetermined angle is in a range so that said leakage angle is approximately 55°.

18. The method as claimed in claim 13 and further comprising:

immersing said body in a liquid; and substantially immersing said transmitter and receiver lens in said liquid.

19. The method as claimed in claim 13 and further comprising:

producing an image of said received leaking acoustic energy.

20. The method as claimed in claim 16 and further comprising:

producing an image of said received leaking acoustic energy.

21. The method as claimed in claim 20 and further comprising:

immersing said body in a liquid; and substantially immersing said transmitter and receiver lens in said liquid.

* * * * *